(12) United States Patent
Duchon et al.

(10) Patent No.: US 8,079,999 B2
(45) Date of Patent: Dec. 20, 2011

(54) FLUID INJECTOR SYSTEM

(75) Inventors: Douglas Duchon, Chanhassen, MN (US); Jason Gerold, Shakopee, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 23 days.

(21) Appl. No.: 12/496,807

(22) Filed: Jul. 2, 2009

(65) Prior Publication Data

US 2010/0004533 A1   Jan. 7, 2010

Related U.S. Application Data

(62) Division of application No. 10/076,836, filed on Feb. 14, 2002, now Pat. No. 7,566,320.

(60) Provisional application No. 60/268,744, filed on Feb. 14, 2001.

(51) Int. Cl.
*A61M 31/00* (2006.01)
(52) U.S. Cl. .................................. 604/500; 600/432
(58) Field of Classification Search .................. 604/432, 604/151–155, 500–522; 600/431–435
See application file for complete search history.

(56) References Cited

U.S. PATENT DOCUMENTS

| | | | |
|---|---|---|---|
| 3,491,749 A * | 1/1970 | Gidlund | 600/432 |
| 3,523,523 A | 8/1970 | Reich et al. | |
| 3,731,679 A | 5/1973 | Braun et al. | |
| 3,739,943 A | 6/1973 | Braun et al. | |
| 4,065,230 A | 12/1977 | Gezari | |
| 4,250,887 A * | 2/1981 | Dardik et al. | 600/432 |
| 4,512,764 A | 4/1985 | Wunsch | |
| 4,535,820 A | 8/1985 | Raines | |
| 4,559,036 A | 12/1985 | Wunsch | |
| 4,854,324 A | 8/1989 | Hirschman et al. | |
| 4,944,726 A | 7/1990 | Hilal et al. | |
| 4,966,199 A | 10/1990 | Ruschke | |
| 4,966,579 A | 10/1990 | Polaschegg | |
| 5,226,886 A | 7/1993 | Skakoon et al. | |
| 5,249,579 A | 10/1993 | Hobbs et al. | |
| 5,254,101 A | 10/1993 | Trombley | |
| 5,267,964 A | 12/1993 | Karg | |
| 5,346,470 A | 9/1994 | Hobbs et al. | |
| 5,349,956 A | 9/1994 | Bonutti | |
| 5,494,036 A | 2/1996 | Uber et al. | |
| 5,515,851 A | 5/1996 | Goldstein | |
| 5,569,181 A | 10/1996 | Heilman et al. | |
| 5,577,503 A | 11/1996 | Bonutti | |
| 5,739,508 A | 4/1998 | Uber | |
| 5,795,333 A | 8/1998 | Reilly et al. | |
| 5,806,519 A | 9/1998 | Evans et al. | |

(Continued)

FOREIGN PATENT DOCUMENTS

EP   0 619 122   10/1994

(Continued)

*Primary Examiner* — Kevin C Sirmons
*Assistant Examiner* — Phillip Gray
(74) *Attorney, Agent, or Firm* — Shumaker & Sieffert, P.A.

(57) ABSTRACT

Fluid injector systems used for a variety of imaging and injection procedures are disclosed. The systems may include separate modules or assemblies that may be located in different rooms of a hospital or imaging facility. Various single use and multiple use components may also be used with the modules or assemblies of the system. In addition, the injector system may include hydraulic and/or pneumatic fluid sources to power the system modules of the present invention.

6 Claims, 21 Drawing Sheets

U.S. PATENT DOCUMENTS

| | | | |
|---|---|---|---|
| 5,808,203 | A | 9/1998 | Nolan et al. |
| 5,840,026 | A | 11/1998 | Uber et al. |
| 5,843,037 | A * | 12/1998 | Uber, III ............ 604/151 |
| 5,873,861 | A | 2/1999 | Hitchins et al. |
| 5,885,216 | A | 3/1999 | Evans et al. |
| 5,920,054 | A | 7/1999 | Uber |
| 5,938,638 | A | 8/1999 | Passariello et al. |
| 5,947,935 | A | 9/1999 | Rhinehart et al. |
| RE36,648 | E | 4/2000 | Uber et al. |
| 6,096,011 | A | 8/2000 | Trombley et al. |
| 6,149,627 | A | 11/2000 | Uber |
| 6,197,000 | B1 | 3/2001 | Reilly et al. |
| 6,306,117 | B1 | 10/2001 | Uber, III |
| 6,317,623 | B1 | 11/2001 | Griffiths et al. |
| 6,339,718 | B1 | 1/2002 | Zatezalo et al. |
| RE37,602 | E | 3/2002 | Uber, III et al. |
| 6,385,483 | B1 | 5/2002 | Uber, III et al. |
| 6,397,098 | B1 | 5/2002 | Uber, III et al. |
| 6,402,717 | B1 | 6/2002 | Reilly et al. |
| 6,440,107 | B1 | 8/2002 | Trombley, III et al. |
| 6,442,418 | B1 | 8/2002 | Evans, III et al. |
| 6,471,674 | B1 | 10/2002 | Emig et al. |
| 6,475,192 | B1 | 11/2002 | Reilly et al. |
| 6,520,930 | B2 | 2/2003 | Critchlow et al. |
| 6,643,537 | B1 | 11/2003 | Zatezalo et al. |
| 6,652,489 | B2 | 11/2003 | Trocki et al. |
| 6,673,033 | B1 | 1/2004 | Sciulli et al. |
| 6,699,219 | B2 | 3/2004 | Emig et al. |
| 6,731,971 | B2 | 5/2004 | Evans, III et al. |
| 6,733,477 | B2 | 5/2004 | Cowan et al. |
| 6,733,478 | B2 | 5/2004 | Reilly et al. |
| 6,743,202 | B2 | 6/2004 | Hirschman et al. |
| 6,889,074 | B2 | 5/2005 | Uber, III et al. |
| 6,901,283 | B2 | 5/2005 | Evans, III et al. |
| 6,939,302 | B2 | 9/2005 | Griffiths et al. |

FOREIGN PATENT DOCUMENTS

| | | |
|---|---|---|
| EP | 0 968 733 | 1/2000 |
| WO | 99/21481 | 5/1999 |

* cited by examiner

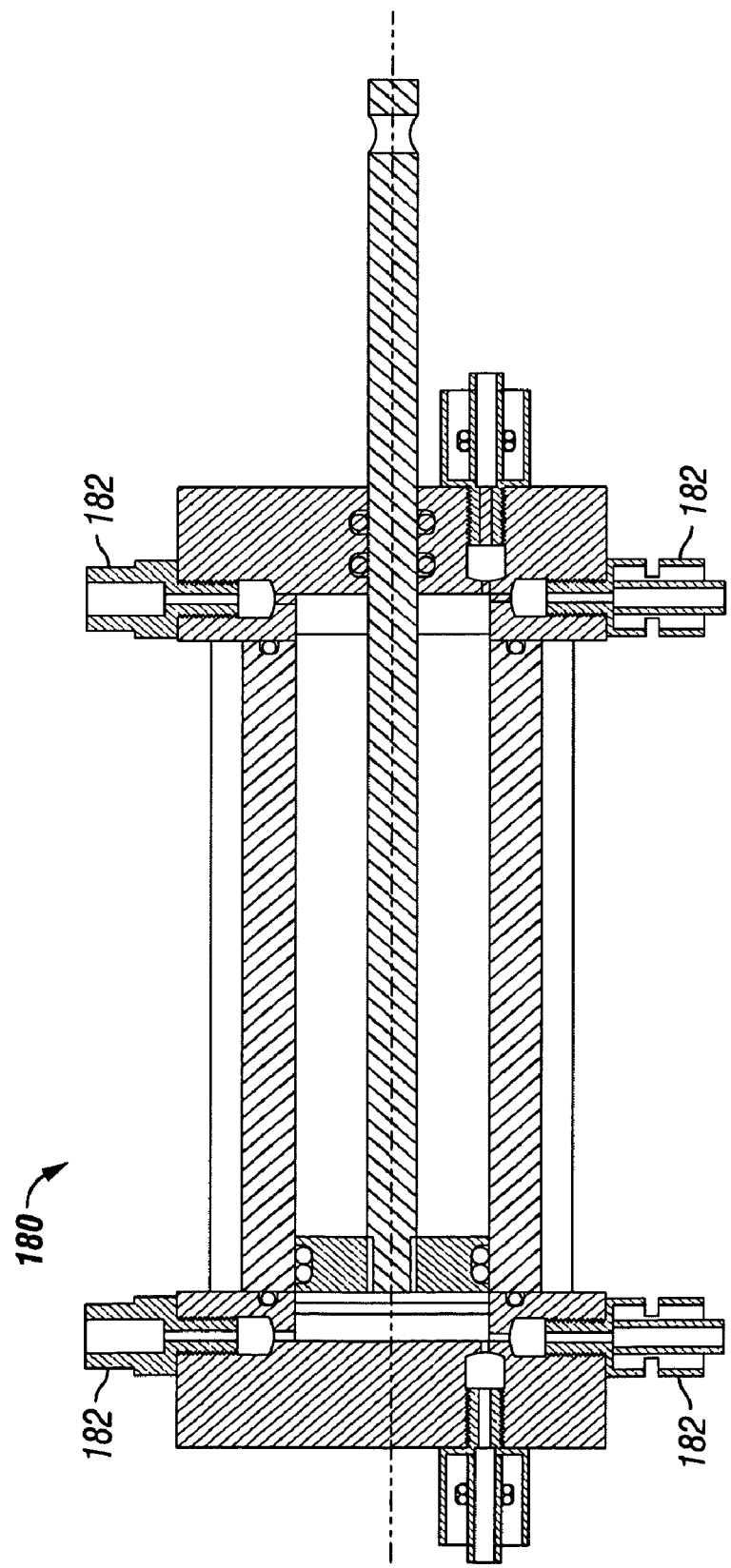

FLUID INJECTOR SYSTEM

CROSS REFERENCE TO RELATED APPLICATIONS

This application is a divisional of U.S. application Ser. No. 10/076,836, filed Feb. 14, 2002, which claims priority to U.S. Provisional Application Ser. No. 60/268,744, filed Feb. 14, 2001, the contents of which are incorporated herein by reference.

BACKGROUND OF THE INVENTION

In many medical environments, a medical fluid is injected into a patient during diagnosis or treatment. One example is the injection of contrast media into a patient to improve computed tomography (CT), angiographic, magnetic resonance (MR) or ultrasound imaging using a powered fluid injection system.

Various manual and automated injection systems used for performing the above-referenced procedures are known in the art. Most current systems include a console and/or control device for controlling the injector. One example of a control device used with an injector system is disclosed in U.S. Pat. No. 5,988,587 to Duchon et al., the disclosure of which is herein incorporated by reference. In addition, a syringe and other disposable components (such as manifold tubing, spikes, etc.) operatively connected to a catheter are also used with conventional injector systems.

In general, during an injection procedure, the syringe is filled by creating a vacuum which causes the fluid (e.g., contrast media) to be suctioned into the chamber of the syringe. Any residual air is ejected from the chamber before connecting the syringe to the patient catheter. Once the system is completely set-up and primed, the syringe is connected to the patient catheter and the contrast media is injected into the target area.

The volume and flow rates of contrast media injections vary depending on patient parameters (such as heart/chamber/vasculature size, patient weight and physical condition) and type of treatment or diagnosis performed. Due to the variability of these parameters, it is often difficult to calculate the precise amount of contrast media needed for a particular patient and procedure. As a result, there exists the potential that the syringe chamber will be either under-filled or over-filled for a particular patient and/or procedure.

If the chamber is under-filled, an insufficient volume of contrast media will be injected into the patient, resulting in a less than optimal image and requiring that the procedure be repeated. This is not only expensive due to the high cost of contrast media, but is also potentially harmful to the patient in view of the additional radiation exposure and contrast dose injected into the patient. Conversely, if the syringe is over-filled, there will be an excess volume of contrast media remaining in the syringe after completion of the imaging procedure. To avoid patient contamination and product adulteration, the remaining volume of contrast media is simply discarded. Although over-filling the syringe avoids the problem of having to repeat the imaging procedure, over-filling wastes contrast media which is costly to hospitals and health care facilities.

Typically, contrast media is supplied in fluid volume containers having a 50 ml, 100 ml, 250 ml or 500 ml capacity. In contrast, patient procedures characteristically require as little as tens of milliliters to as much as hundreds of milliliters of fluid per procedure. The limited container volumes in conjunction with the variability associated with patient procedures often result in wasted fluid. For example, if a procedure requires 150 ml of fluid and a 250 ml container is used, the amount of fluid remaining in the container at the end of the procedure is discarded due to possible cross-contamination and fluid-crystallization issues. The discarded, unused portion not only wastes fluid, but also significantly contributes to increased hospital costs.

In addition to cost issues, the medical community is also faced with contamination problems associated with imaging procedures and, more particularly, the injector systems used to dispense the fluids. For example, the syringe, tubing and ancillary injector components used during imaging procedures are in fluid-communication with the patient. As a result, these items must be discarded after each case in order to avoid patient and/or product contamination, a potential risk confronting all products used during invasive procedures. Another reason for disposing of these items after a single use is that the majority of the imaging components are made of materials that are incompatible with state-of-the-art cleaning and resterilization procedures and, therefore, cannot be reused.

Although presently available injector systems are well accepted by the medical profession and function as required, it is desirable to have a more cost-effective injector system that is also safe and efficacious to use. In particular, it is desirable to have an injector system with continuous flow capability, thereby eliminating the need to refill the syringe during an injection procedure. It is also preferred that the system accurately and precisely control fluid injections from both near and remote locations. It is also essential that the contrast media/fluid supply remain contamination-free during each use. In addition, it is desirable to have an injection system with both disposable and reusable accessory components. Further, it is preferred that the system perform both diagnostic and non-diagnostic procedures, such as x-ray procedures, CT scanning, magnetic resonance (MR) imaging, ultrasonic imaging, infrared, UV/visible light fluorescence, Raman spectroscopy, microwave imaging, angioplasty, saline ablation, guided interventional procedures fully executable in the sterile field, etc., and is capable of using a variety of fluids, such as contrast media, saline, flushing fluids, etc.

BRIEF SUMMARY OF THE INVENTION

In view of the foregoing, it is an object of the present invention to provide an injector system that addresses the obstacles and disadvantages associated with conventional fluid injection practices.

A further object of the present invention is to provide an injector system that is cost-effective, safe and efficacious to use.

A further object of the present invention is to provide a continuous flow injector system that can also accommodate one or more fluids types having various volumes, concentrations, viscosities, etc.

A further object of the present invention is to provide a system wherein the fluid supply remains contamination free.

A further object of the present invention is to provide an injector system for use in magnetic resonance imaging procedures. The injector system includes a main console, including at least one first cylinder assembly, a hand held control in communication with the main console and at least one second cylinder assembly in fluid communication with the first cylinder assembly. In addition, the injector system also includes at least one syringe assembly in communication with the second cylinder assembly, wherein the main console, first cylinder assembly and hand held control are in a control room and the second cylinder assembly and syringe assembly are in an imaging room.

Another embodiment of the present invention is to provide an injector system for use in magnetic resonance imaging procedures comprising a main console, including at least one first cylinder assembly; a hand held control in communication with the main console, and at least one hydraulic motor in fluid communication with the first cylinder assembly. In addition, the injector system also includes at least one peristaltic pump in communication with the hydraulic motor, wherein the main console, first cylinder assembly and hand held control are in a control room and the hydraulic motor and peristaltic pump are in an imaging room. Alternatively, a gear cartridge may be used in place of the peristaltic pump.

A further embodiment of the present invention is to provide a method of injecting a first fluid into a patient during a magnetic resonance imaging procedure. The method includes providing a first cylinder assembly in a control room of an imaging facility, wherein the first cylinder assembly is in communication with an injector console, and providing a second cylinder assembly and a syringe assembly in a patient room of an imaging facility, wherein the second cylinder assembly is in communication with the first cylinder assembly and syringe assembly, and providing a second fluid in communication with the first cylinder assembly and second cylinder assembly. The method also includes driving the first cylinder assembly with a motor, driving the second cylinder assembly with the second fluid provided by the first cylinder assembly, driving the syringe assembly with the second cylinder assembly, and injecting a patient with the first fluid using the syringe.

A further embodiment of the invention includes a method of injecting a first fluid into a patient during a magnetic resonance imaging procedure. The method includes providing a cylinder assembly in a control room of an imaging facility, wherein the cylinder assembly is in communication with an injector console, and providing a hydraulic motor and a peristaltic pump in a patient room of an imaging facility, wherein the hydraulic motor is in communication with the cylinder assembly and peristaltic pump. The method also includes providing a second fluid in communication with the cylinder assembly and hydraulic motor, driving the cylinder assembly with a motor, and driving the hydraulic motor with the second fluid provided by the cylinder assembly. Further, the method includes driving the peristaltic pump with the hydraulic motor and injecting a patient with the first fluid using the peristaltic pump. Alternatively, a gear cartridge may be used in place of the peristaltic pump.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

FIGS. 14A-D illustrate a syringe assembly in accordance with an embodiment of the present invention;

DETAILED DESCRIPTION OF THE INVENTION

Figure 1:
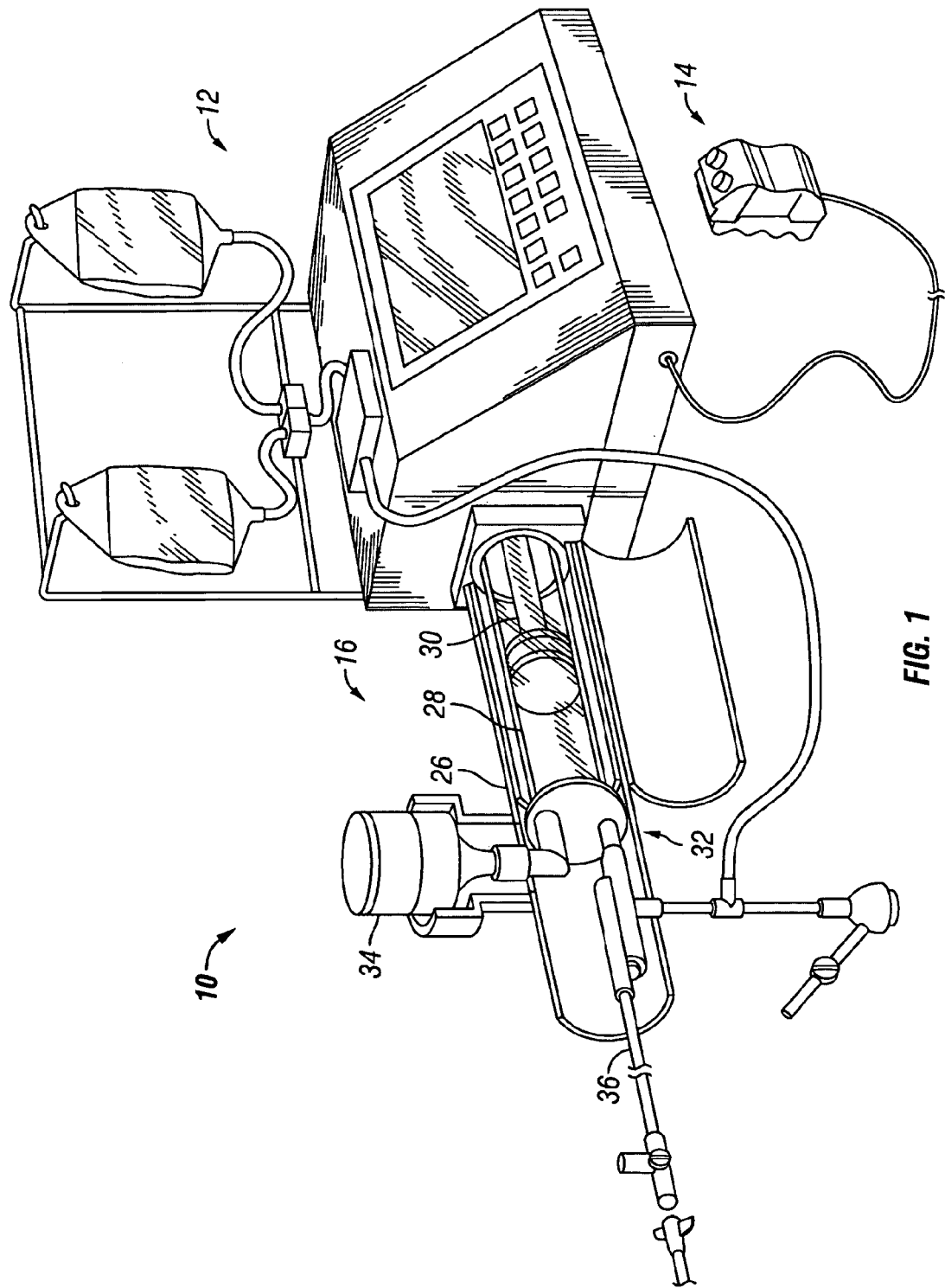
FIG. 1 is a perspective view of an angiographic injector system in accordance with an embodiment of the present invention.

Referring to FIG. 1, an embodiment of an injector system 10 used to inject fluid into a blood vessel under interactive physician control in accordance with the present invention includes a main console 12, a hand held control 14 and a syringe holder subassembly 16. An example of an injector system 10 included within the scope of the present invention is disclosed in U.S. Pat. No. 6,221,045 to Duchon et al., and is hereby incorporated by reference in its entirety into the present application. It should be noted that the description and figures of the present application are meant to be illustrative only and not limiting. In addition, references to a user interface, user interface/console and similar user control devices are intended to include components similar to the main console and hand-held/remote control, as previously described. Further, the hand-held/remote control may be located in a control room or the same room as the patient and, further, may also be used in the sterile field. As such, a practitioner/user of the device may simultaneously control the injector system and perform guided interventional procedures, all within the sterile field.

Although some of the illustrated and described embodiments may relate to angiographic injectors and procedures, any of a variety of injector systems, procedures and methods of use including, but not limited to, manual injector systems, automated injector systems, x-ray procedures, CT scanning, magnetic resonance imaging (MRI), ultrasonic imaging, infrared, UV/visible light fluorescence, Raman spectroscopy, microwave imaging, angioplasty, saline ablation, guided interventional procedures fully executable in the sterile field, endoscopy and hysteroscopy are also included within the scope of the claimed invention.

Figure 2:
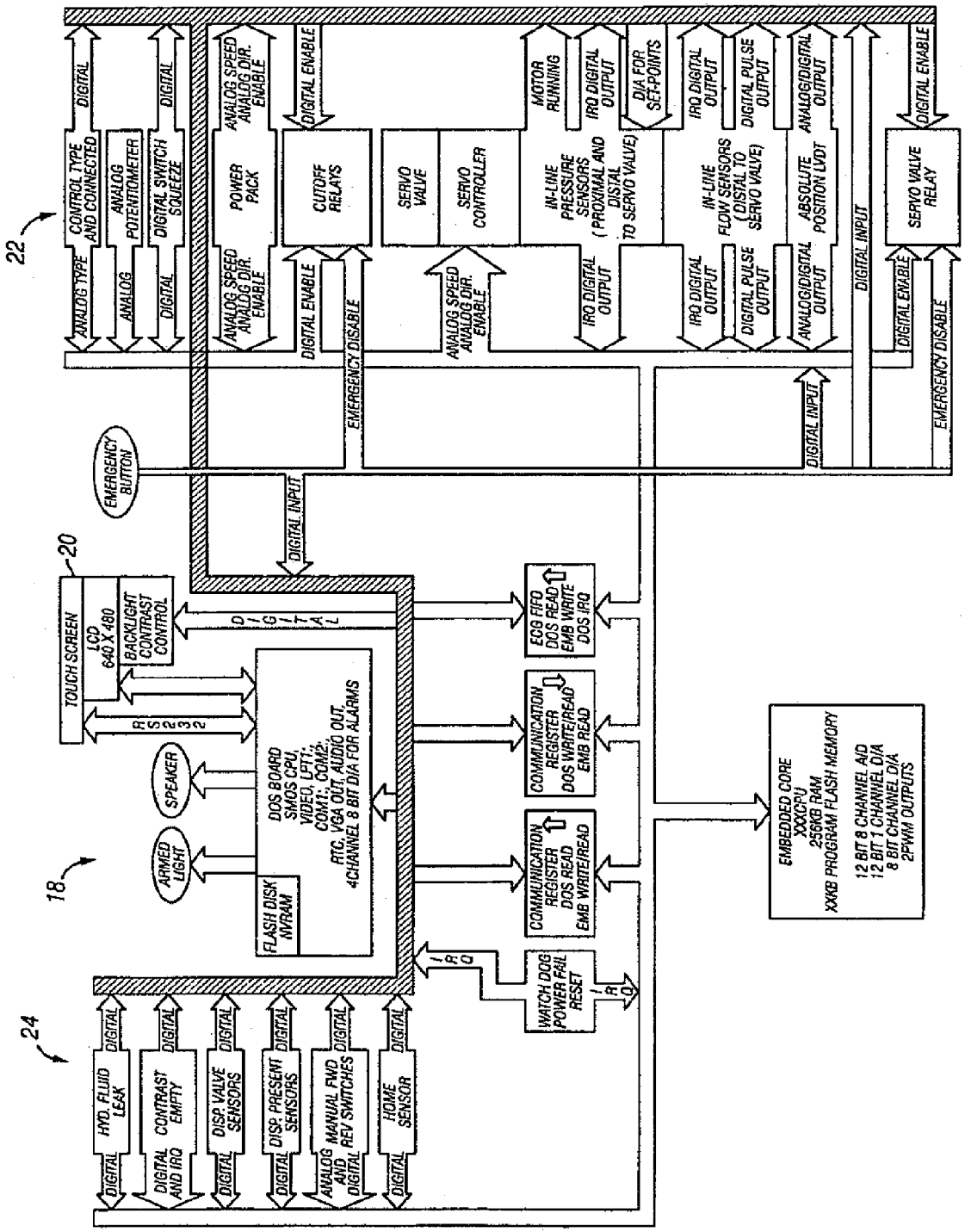
FIG. 2 is a flow chart illustrating signal or communication paths of an injector system in accordance with an embodiment of the present invention.

Each subassembly or module of the injector system 10 performs a variety of operations and maintains communication with the other subsystems to ensure proper functioning of the device. For example, as shown in FIG. 2, the control panel module 18 includes a user interface 20 through which the user may enter control settings and monitor the operational state of the system. The user may also enter command signals, to control fluid flow or injection rates, and monitor (e.g., view) the operational state of the system via the hand control module 22. In general, the command signals are sent to various processing devices and components that actuate the desired injection operation via the mounting chamber module 24. Additional examples of internal circuitry diagrams for the injector modules 18,22,24 and overall system design may be found in U.S. Pat. No. 6,004,292 and U.S. Pat. No. 6,221,045, which are hereby incorporated by reference in their entirety into the present application.

As shown in FIG. 1, the syringe holder subassembly 16 includes a syringe holder 26 that houses a syringe body 28. Located within the syringe body 28 is a detachable syringe plunger 30 that is connected to and driven by a motor (not shown) located within the console 12. During use, the plunger 30 is initially driven to its furthest forward position or toward the distal end 32 of the syringe body 28. This will expel to the atmosphere the majority of air which is located within the syringe body 28. The plunger 30 is then retracted (toward the open end of the syringe 28), which creates a vacuum within the syringe body 28, thereby drawing fluid from the reservoir 34 into the syringe body 28. Once the syringe 28 is filled with fluid, the plunger 30 is once again driven forward. Additional examples of the fluid fill procedure may be found in currently pending U.S. patent application Ser. No. 09/909,734 and U.S. patent application Ser. No. 09/577,906, which are hereby incorporated by reference in their entirety into the present application.

The movement of the plunger 30 creates hydraulic pressure to force the fluid out of the syringe body 28, through the tubing 36 and catheter (not shown) and into the patient (not shown). Images of the fluid as it travels to the target site within the patient are generated using low doses of radiation or x-rays. Operation and monitoring of the injection procedure is performed by a user of the device, who is generally in the same room (e.g., catheterization laboratory or O.R. suite) with the patient and injector system 10.

Figure 3A:
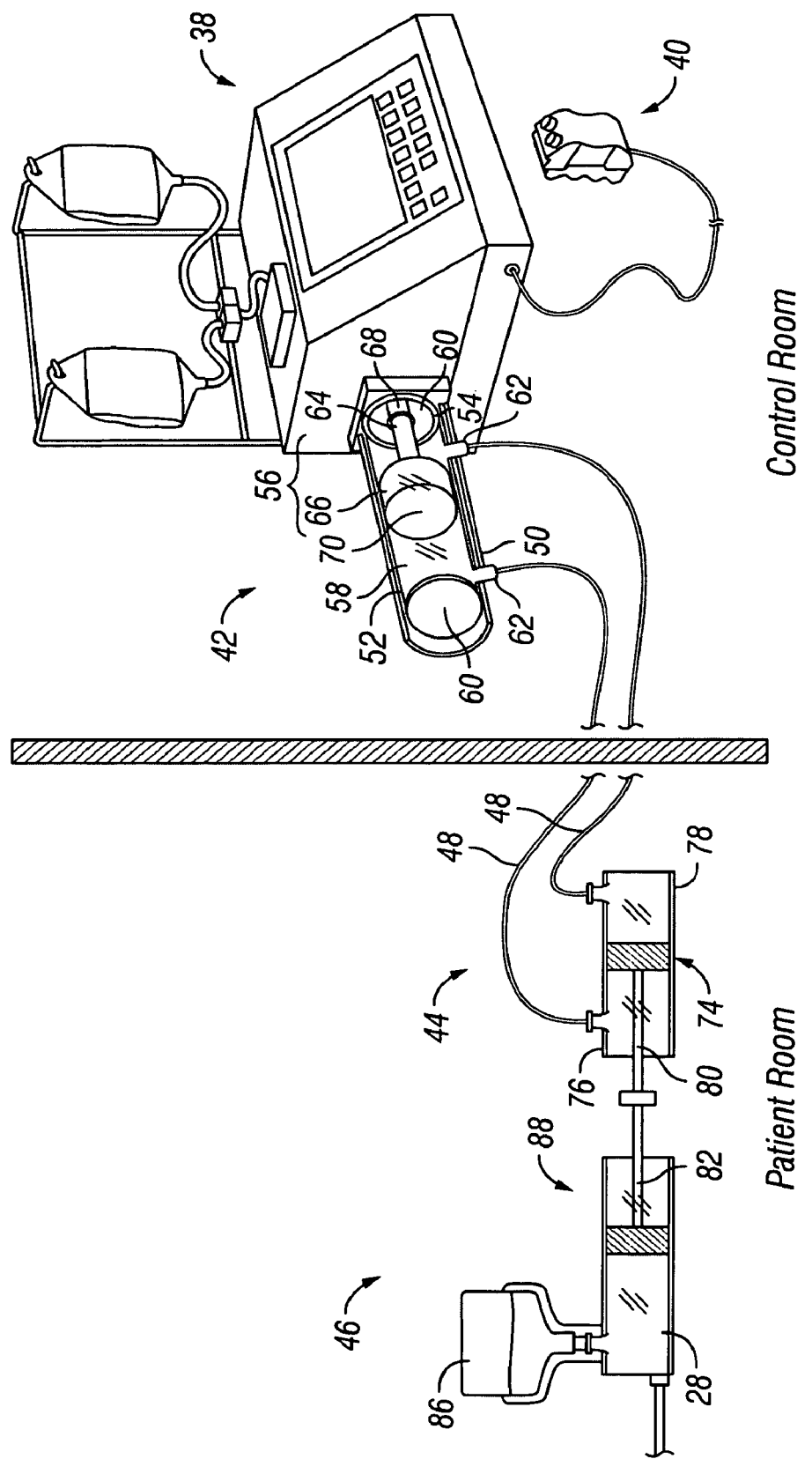
FIGS. 3A and 3B are perspective views of a remote injector system in accordance with an embodiment of the present invention.
Figure 3B:
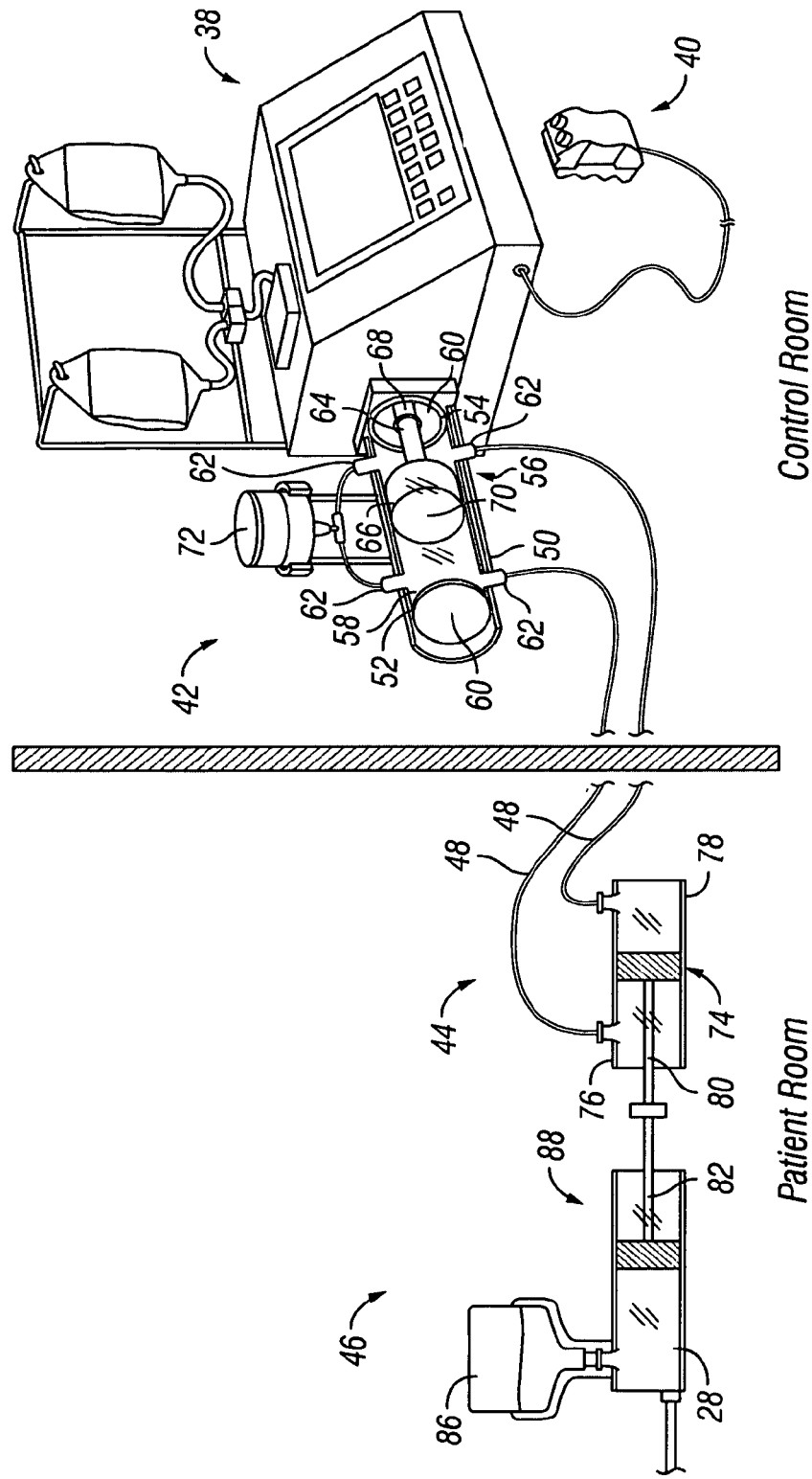

In an alternate embodiment of the present invention, the injector system 10 includes a main console 38, a hand held control 40, a first cylinder assembly 42, a second cylinder assembly 44 and a syringe assembly 46. As shown in FIGS. 3A and 3B, the main console 38, hand held or remote control 40 and first cylinder assembly 42 are located in a control room of a hospital or imaging facility. The second cylinder assembly 44 and syringe assembly 46, which are in fluid communication with the injector system via tubing 48, are located in the patient or imaging room of the facility. In an alternate embodiment of the invention (not shown), the remote control 40 may be located in the same room as the patient and, further, may also be used in the sterile field. As such, a practitioner/user of the device may simultaneously control the injector system and perform guided interventional procedures, all within the sterile field. As explained in further detail below, this particular system design provides a low cost, accurate and user-friendly alternative to conventional manual injection systems.

As shown in FIG. 3A, the main console 38, hand held/remote control 40 and syringe body 28 are similar to those used with the injector system 10 referenced above. However, a first cylinder assembly 42 is positioned at the location of the syringe body 28 shown in FIG. 1. The first cylinder assembly 42, a second cylinder assembly 44 and tubing 48 form a pre-filled, sealed, closed-loop system located between the main console 38 and the syringe assembly 46. The closed-loop system may also include an air vent and fill port (not shown) for system venting and fluid filling operations. In general, the first cylinder assembly 42 includes a cylindrically shaped body 50, having a distal end 52 and a proximal end 54, and a plunger 56. A curved side-wall 58 and two end walls 60 form the body and pumping chamber 50 of the first cylinder assembly 42. The end walls 60, located at both the distal and proximal ends 52,54 of the cylinder body 50, are generally flat-faced surfaces that are in perpendicular alignment with the axis of the first cylinder assembly 42. In addition, one or more ports 62 located near the ends 52,54 of the first cylinder assembly 42 provide an inlet and/or outlet for fluid flow.

In one embodiment of the invention, the cylinder body 50 is made of a transparent or translucent material through which the operator can view the location of the plunger 56 and any fluid or air in the pumping chamber 50. Suitable materials for the cylinder body 50 include, but are not limited to, polycarbonate, polyvinyl chloride (PVC), polypropylene, polystyrene, polyethylene terephthalate (PET), styrene acrylonitrile copolymer (SAN), clear acrylonitrile-butadiene-styrene (ABS) copolymer, polymethyl pentane and combinations thereof. Alternatively, the cylinder body may be made of an opaque material or combinations of opaque, transparent and/or translucent materials.

Housed within the cylinder body 50 is a plunger 56 that includes a rod-shaped shaft 64, having a distal end 66 and a proximal end 68, and a disc-shaped wiper 70. The shaft 64 may be made from a variety of materials including, but not limited to, aluminum, stainless steel, titanium, ceramics, alloy steels, polymers, and combinations thereof. Suitable wiper materials include silicone, nitrile, latex, nitrile rubber (NBR), buna rubber, polyisoprene and other compatible materials well known in the art.

In general, the distal end 66 and proximal end 68 of the shaft 64 are attached to or in communication with the wiper 70 and an actuator (not shown), respectively. The wiper 70 is configured to maintain an airtight seal with the inside surface of the side-wall 58 of the cylinder body 50 and, thereby, forms sub-chambers within the pumping chamber 50 of the first cylinder assembly 42. The actuator, housed within the console 38, drives the plunger 56, in particular the wiper 70, in reciprocal motion between positions adjacent to the distal and proximal ends 52,54 of the first cylinder assembly 42. As such, movement of the wiper 70 forces fluid or air out of a first sub-chamber via a port 62 and also creates a vacuum that draws either fluid or air through a port 62 and into a second sub-chamber of the first cylinder assembly 42.

The second cylinder assembly 44 of the injector system 10 is similarly configured to that of the first cylinder assembly 42. However, plunger movement in the first cylinder assembly 42 hydraulically controls movement of the plunger assembly 74 within the second cylinder assembly 44. For example, proximal movement of the plunger assembly 56 forces fluid out of the proximal sub-chamber of the first cylinder assembly 42, through the second tubing set 48 and into the proximal sub-chamber of the second cylinder assembly 44. The force of the fluid entering the proximal sub-chamber of the second cylinder assembly 44 causes movement of the plunger assembly 74 toward the distal end of the second cylinder assembly 44. Movement of the plunger assembly 56 toward the distal end of the first cylinder assembly 42 forces fluid from the distal sub-chamber of the first cylinder assembly 42, through the second tubing set 48 and into the distal sub-chamber of the second cylinder assembly 44. The force of the fluid entering the distal sub-chamber of the second cylinder assembly 44 causes movement of the plunger assembly 74 toward the proximal end of the second cylinder assembly 44. Additional reciprocating movement of the plunger assembly 56 in the first cylinder assembly 42 causes additional reciprocating movement of the plunger assembly 74 in the second cylinder assembly 44. Plunger movement and positioning is accurately maintained since the fluid and tubing 48 are incompressible and fairly rigid, thereby causing no or limited hysteresis and deflection. In addition, the system may also include a home position and position sensors to accurately determine wiper location when no injection procedure is being performed.

In an alternate embodiment of the present invention, shown in FIG. 3B, the injector system 10 may also include a fluid source or reservoir 72 in communication with the first cylinder assembly 42. For this embodiment of the invention, the previously described closed-loop system is not pre-filled, thereby requiring a fluid source 72 to initially fill the closed-loop system with fluid. Pressure differentials created by movement of the plunger 56 cause fluid from the reservoir 72 to flow through a first tubing set 48 and into the sub-chambers of the first cylinder assembly 42. Additional plunger movement forces the fluid out of the sub-chambers, through a second tubing set 48 and into the second cylinder assembly 44. In one embodiment of the invention, one or more valves (not shown) may also be included to control fluid flow and venting through the various tubing sets.

Referring to FIG. 3A, the plunger shaft 80 of the second cylinder assembly 44 is in communication with a plunger shaft 82 housed within the syringe body 28. The syringe assembly 46 and reservoir 86 illustrated in FIG. 3A is similar in design and function to the syringe assembly 28 and reservoir 34 illustrated in FIG. 1. However, the plunger 88 of the syringe assembly 46 of FIG. 3A is directly driven by the linear motion and force of the above-referenced fluid hydraulic system, rather than by a motor or actuator as with the previously described injector system of FIG. 1. Reciprocal motion of the syringe plunger 88 creates pressure differentials and driving forces, similar to those previously described with respect to the cylinder assembly. As such, fluid from the reservoir 86 is drawn into and subsequently forced out of the syringe body 28, through a catheter and into the patient, thereby producing the desired injection procedure.

In an alternate embodiment of the present invention, the syringe assembly 46 and second cylinder assembly 44 are made of non-ferromagnetic materials. Examples of suitable non-ferromagnetic materials include, but are not limited to, ceramics, aluminum, austenitic stainless steel, brass, bronze and polymers. As such, unlike conventional injection systems (that are prohibitively configured for MRI and similar procedures), the injector system of the present invention may be used for imaging and other related procedures that use, for example, electro-magnetic fields. MRI procedures utilize strong magnetic fields generated from large bore magnets to create a three-dimensional image of a patient. The magnetic fields produced by these large bore magnets are strong enough to pick up and pull large ferromagnetic items into the bore of the magnet, potentially destroying the magnet and harming the patient. In addition, the magnetic fields also cause interference with other electronic devices that are in the same room as the magnet. As such, conventional automated and some manual injection systems, which typically include ferromagnetic components, cannot be used for MRI procedures. However, since only the non-ferromagnetic components of the injector system of the present invention are in the same room with the patient and the magnetic field, the system of the present invention is a practical, safe and effective solution for MRI and other related procedures.

Figure 4:
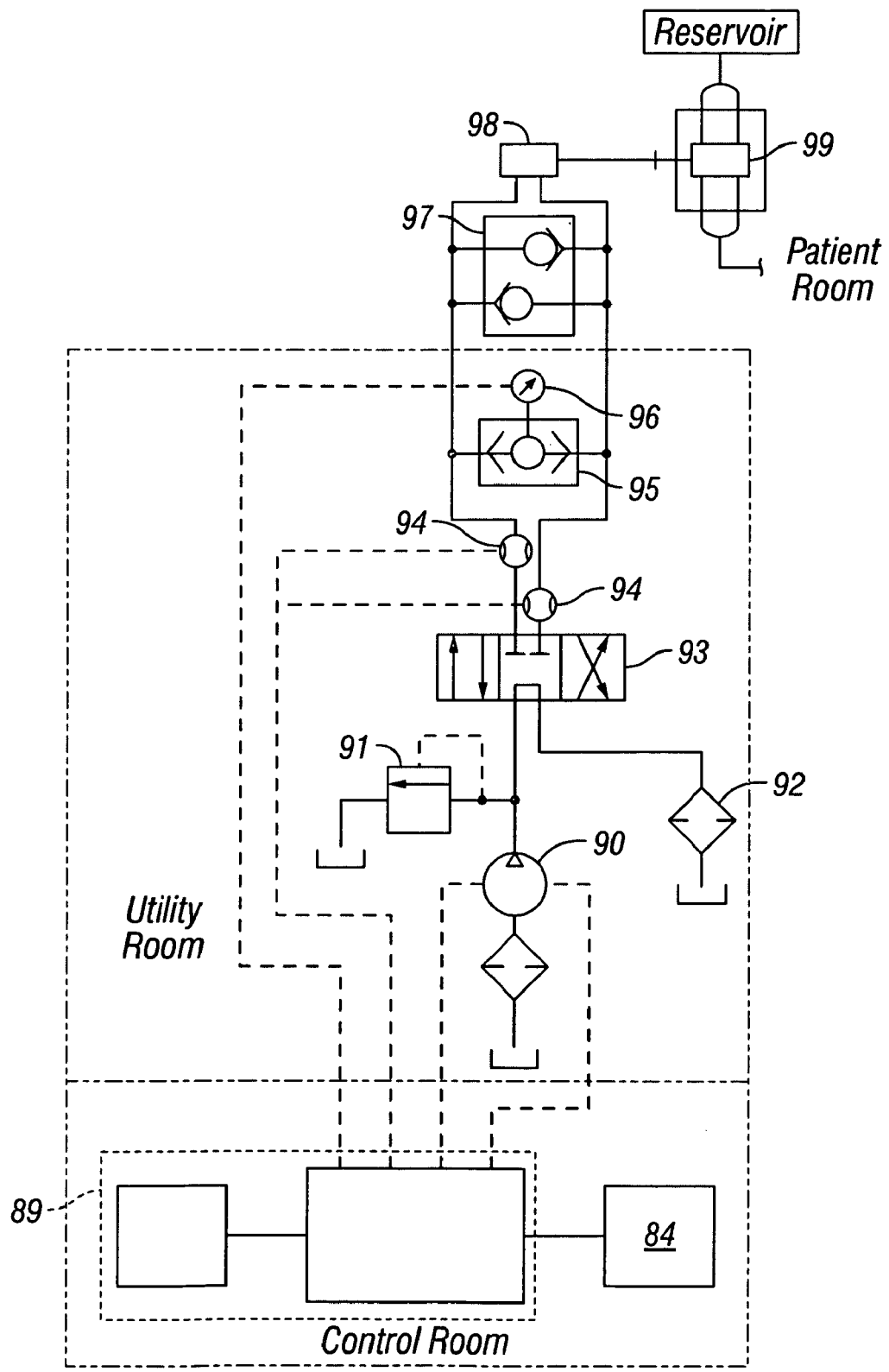
FIG. 4 is a schematic view of a remote injector system in accordance with an embodiment of the present invention.

In another embodiment of the invention, a conventional hydraulic system may be used in place of the main console 38, hand-held control 40 and first cylinder assembly 42 illustrated in FIGS. 3A and 3B. As shown in FIG. 4, the hydraulic system may include a user interface 84 and control unit 89 located in a control room of a hospital or imaging facility. The user-interface 84 may include components similar to the main console 38 and hand-held control 40. Further, as previously described, the hand-held/remote control 40 may be located in the same room as the patient and, further, may also be used in the sterile field. As such, a practitioner/user of the device may simultaneously control the injector system and perform guided interventional procedures, all within the sterile field. Additional system components, including a hydraulic pump 90, pressure relief valve 91, filter 92, servo valve/valve driver 93, flow rate sensors 94, shuttle valve 95 and pressure sensor 96, may be located in a utility room of a hospital or imaging facility. Further, a relief valve 97, cylinder 98 and syringe 99 may also be located in the same room as the patient.

Referring to FIG. 4, the user interface 84 and control unit 89 function similar to those previously described. During use, a user of the device enters the desired injection parameters via the user interface 84. The user commands are transferred to the control unit 89 and converted to appropriate system signals. The signals are transferred to the hydraulic pump 90 which converts mechanical power to fluid power. A variety of pumps including, but not limited to, piston-type pumps, radial pumps, plunger pumps, gear pumps and centrifugal pumps may be used with the device of the present invention. As the fluid travels from the pump 90 to the cylinder 98, various system components control fluid flow and pressure in the system. In general, fluid flow direction between the pump 90 and cylinder 98 is controlled by the servo valve/valve driver 93. One or more flow rate sensors 94, located downstream from the servo valve/valve driver 93, translate fluid flow through the hydraulic tubing into a linear displacement of the plunger in the cylinder 98. Further, pressurized fluid fed into the cylinder 98 is converted into linear motion and force that drives the syringe 99 that is used to inject fluid, such as contrast media, into the patient.

Pressure in the hydraulic tubing of the system is also monitored and controlled via the pressure sensor 96 and shuttle valve 95. In particular, the shuttle valve 95 monitors the hydraulic tubing in fluid communication with the cylinder 98 to obtain pressure readings in the cylinder 98. If there is a malfunction, such as increased pressure in the system, the increased pressure triggers the pressure relief valve 91 which re-routes fluid to the pump reservoir. Before fluid re-enters the pump reservoir, the fluid flows through a filter 92 to remove any particulates. The cross over relief valve 97 also functions to equalize pressure within the hydraulic tubing. For example, if fluid pressure is too high, the valve 97 opens and relieves the pressure differential between the tubing lines. The cross over relief valve 97 may be set to a predetermined pressure to trigger opening of the valve 97.

A variety of fluids may be used with the injector system of the present invention. Examples of applicable fluids used with the hydraulic components include, but are not limited to, water, saline, water-based fluids, conventional oil hydraulic fluids, ethylene glycol or any low compressible fluid. By definition, fluid power includes both hydraulics and pneumatics. As such, pressurized air may also be used with the system of the present invention, as described in further detail below. Injection fluids (i.e., fluids delivered to the patient) such as contrast media, saline, drugs, medicaments and other injection fluids known in the art may also be used with the present invention.

Figure 5:
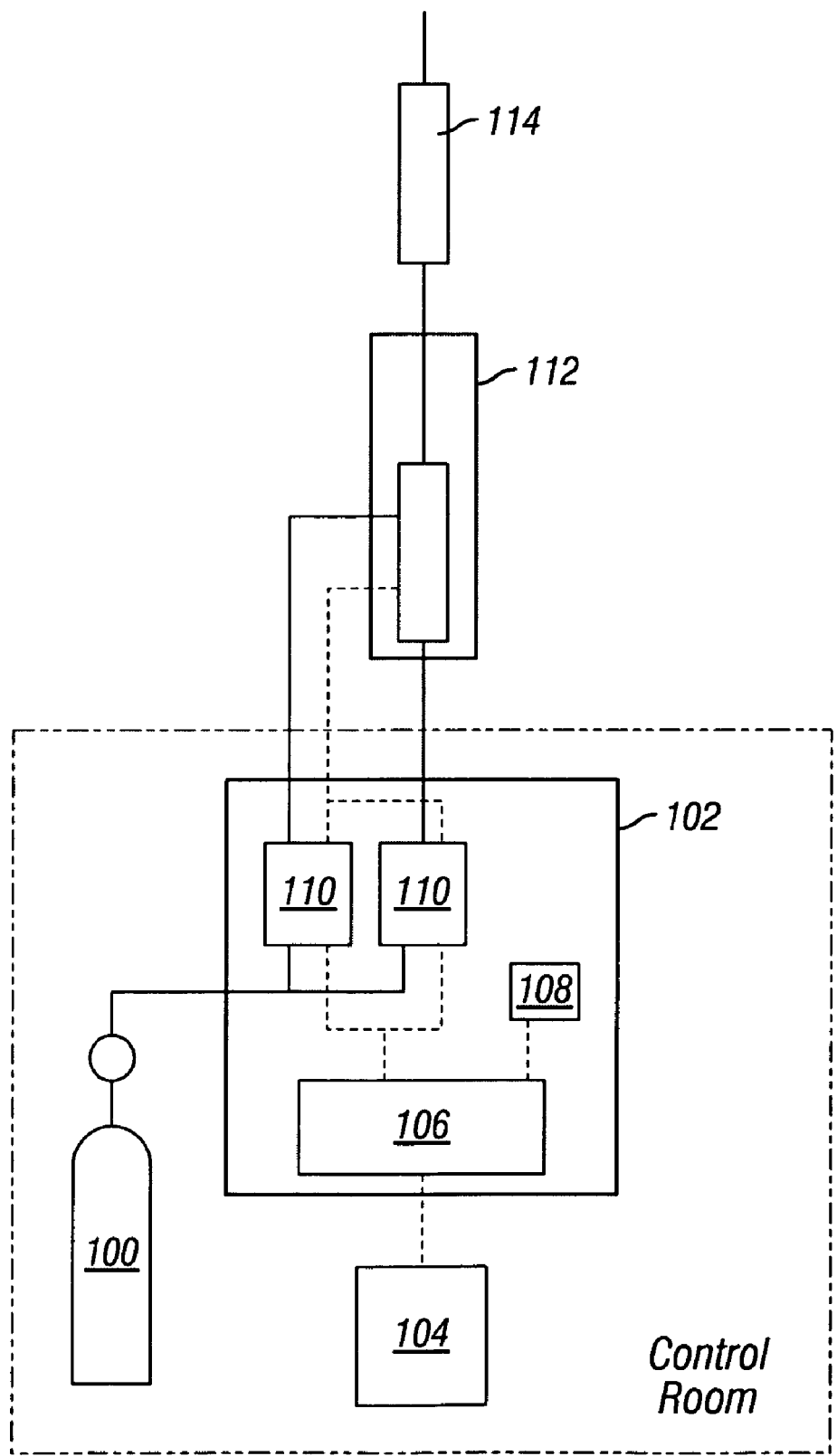
FIG. 5 is a block diagram illustrating an injector system in accordance with an embodiment of the present invention.

In an alternate embodiment of the present invention, a pneumatic pump may be used in place of the above-referenced hydraulic pump. As shown in FIG. 5, the fluid reservoir 100 contains a supply of pressurized carbon dioxide ($CO_2$), compressed air or other type of gas that drives the pneumatic pump 102. A user interface/console 104 controls the pump and it's associated controller 106, power supply 108, servo control valves 110 and other related system components. The user-interface/console 104 may include components similar to the main console and hand-held/remote control, as previously described. Further, the hand-held/remote control 40 may be located in the same room as the patient and, further, may also be used in the sterile field. As such, a practitioner/user of the device may simultaneously control the injector system and perform guided interventional procedures, all within the sterile field.

During use, a user of the device enters the desired injection parameters via the user interface/console 104. The user commands are transferred to the controller 106 that converts the commands into appropriate system signals. The signals from the controller 106 are then transferred to the control valves 110, which control fluid flow into and out of the pump assembly 102. As such, air from the reservoir 100, pumped through the control valves 110 and cylinder assembly 112, generates linear motion or force that drives the syringe assembly 114 and, thus, regulates fluid flow into the patient.

Figure 6A:
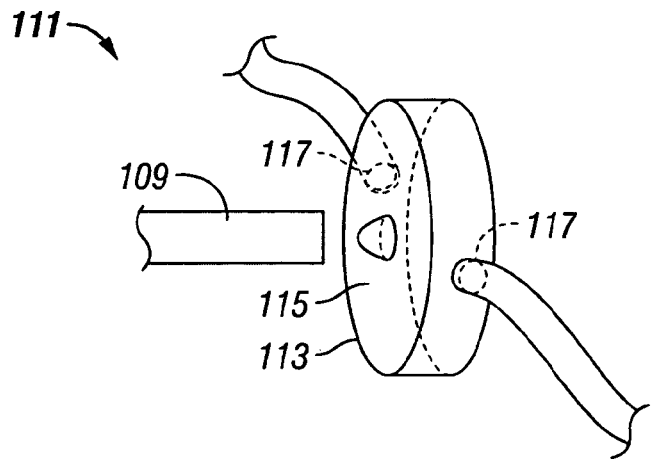
FIGS. 6A-6C illustrate a diaphragm pump in accordance with an embodiment of the present invention.
Figure 6C:
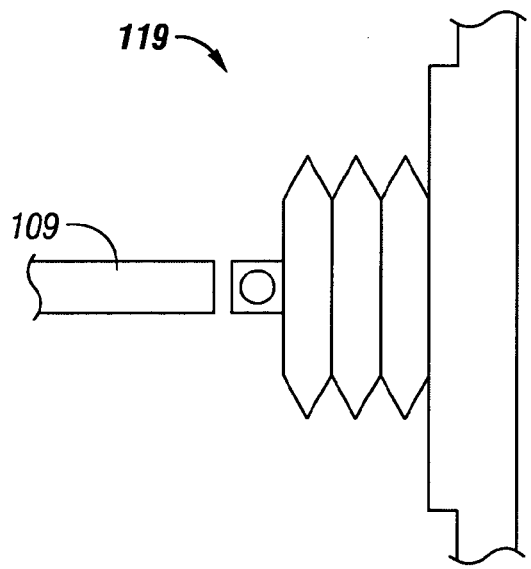
Figure 6B:
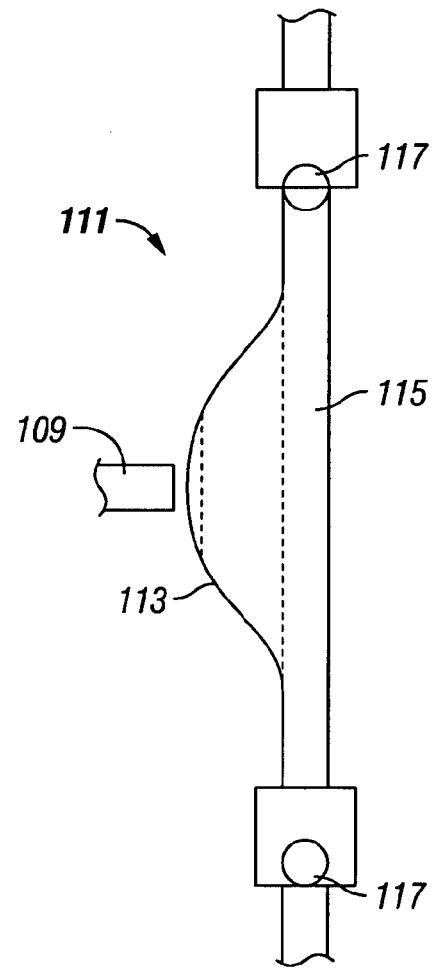

In an alternate embodiment of the invention, the syringe of the present invention is replaced with a diaphragm or bellows. As shown in FIGS. 6A and 6B, the distal end of the plunger shaft 109 of the second cylinder assembly (not shown) is in communication with a diaphragm 111. In general, the diaphragm 111 is configured to include a flexible cover or membrane 113 that defines a passage 115 and two ports 117 in fluid communication with the passage 115. One port 117 of the diaphragm 111 is in fluid communication with a fluid reservoir (not shown) that contains, for example, contrast media. The other port 117 of the diaphragm 111 is in fluid communication with the patient (not shown).

During use, applications of linear, reciprocal motion or force from the plunger shaft 109 compress and release the flexible membrane 113 of the diaphragm 111, which creates pressure differentials within the passage 115. The pressure differentials draw in fluid from the reservoir, through a port 117 and into the passage 115. In addition, the pressure differentials also force or pump out fluid from the passage 115, through the other port 117 and to the patient. One or more fluid control valves may be used with the diaphragm of the present invention to control fluid flow through the system.

Alternate embodiments of the invention may include two or more diaphragms, with each diaphragm having two or more ports, used to transport one or more fluids through the system. In addition, alternate diaphragm 111 configurations, such as the bellows 119 shown in FIG. 6C function similar to the diaphragm 111 and are also included within the scope of the present invention.

Figure 7A:
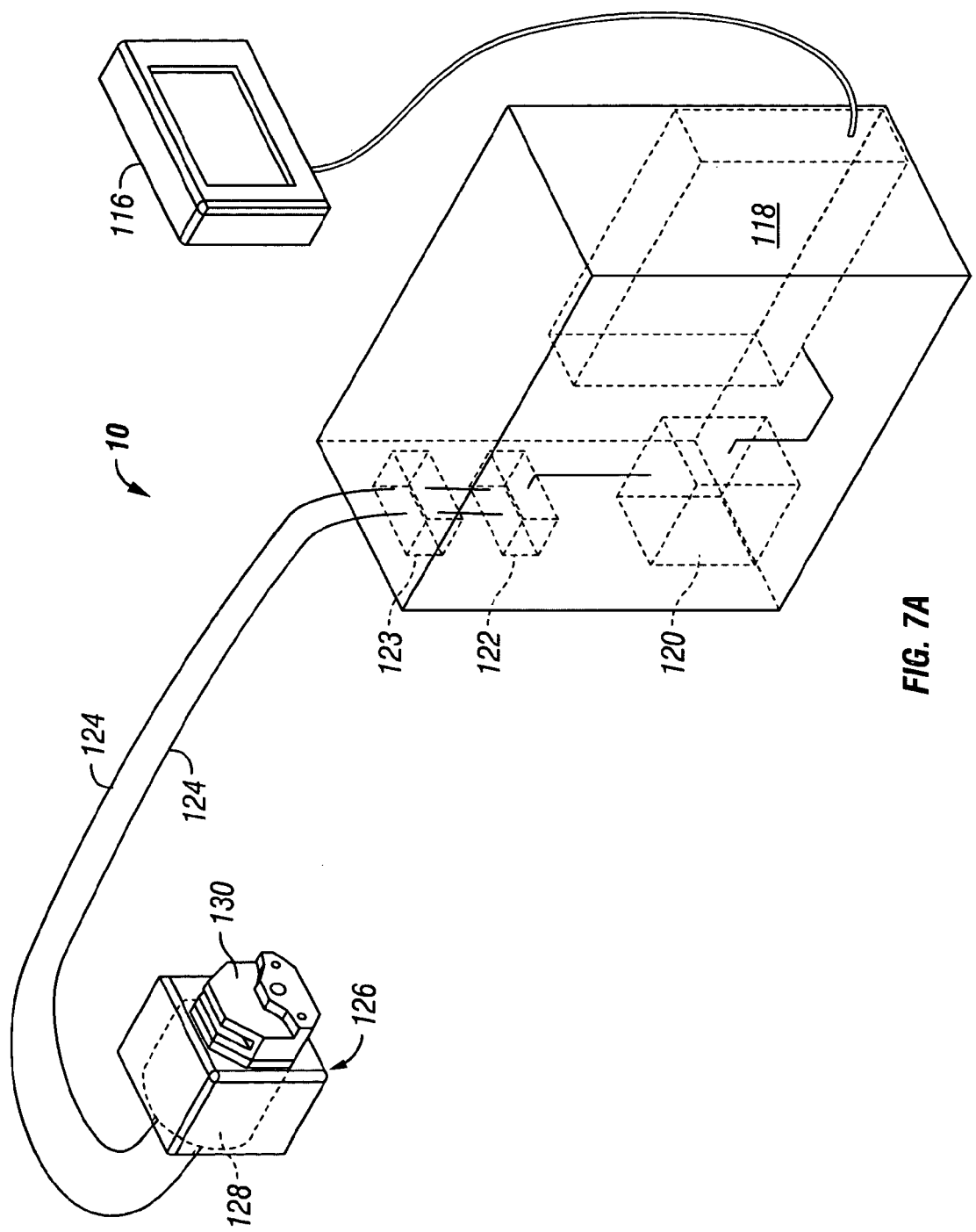
FIG. 7A is a partial block diagram and perspective view of an injector system in accordance with an embodiment of the present invention.

As is well known in the art, both hydraulic and pneumatic fluid powered systems may generate either linear forces (as previously described) or rotary forces. Therefore, in an alternate embodiment of the invention, the hydraulic or pneumatic system is used to generate rotary forces to drive a peristaltic pump or gear pump of the injector system. As shown in FIG. 7A, the injector system 10 includes a user interface 116, control module 118, hydraulic or pneumatic components 120, control valves 122, fluid sensors 123, fluid reservoir (not shown), tubing 124 and a hydraulic motor/peristaltic pump 128. It should be noted that this embodiment of the invention may not require a syringe. When pressurized fluid is fed through the hydraulic motor 128, the hydraulic motor 128 produces rotary torque which rotates a rotor (not shown) of the peristaltic pump 130. Rotation of the rotor causes two or more rollers of the rotor to compress the tubing, thereby drawing in fluid from the reservoir and transporting the fluid through the tubing in the direction of the rotor's rotation. Fluid flows through the tubing and to the target site in the patient (not shown).

Figure 7B:
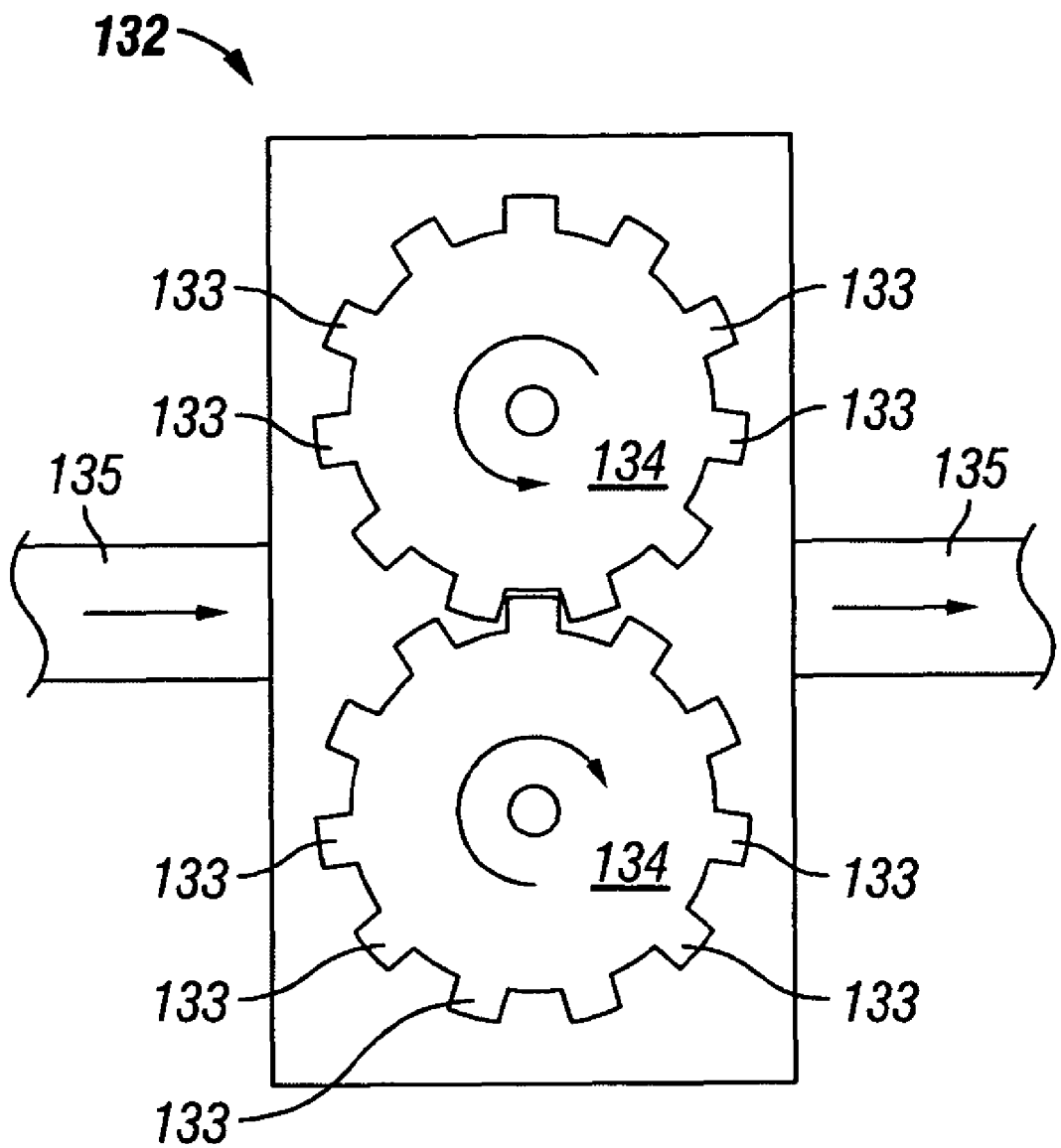
FIG. 7B is a sectional view of a gear cartridge in accordance with an embodiment of the present invention.

Alternatively, a gear cartridge 132 may be used in place of the peristaltic pump 130. As shown in FIG. 7B, rotation of the rotor (not shown) causes two or more gears 134 to rotate. Rotation of the gears 134 causes fluid to be drawn into the cartridge 132 and forced out of the cartridge 132 via movement of the gear teeth 133. As such, the gear teeth 133 function as paddles or vanes to transport fluid in the direction of gear rotation. The fluid then flows through the tubing 135 and into the patient (not shown).

Figure 8A:
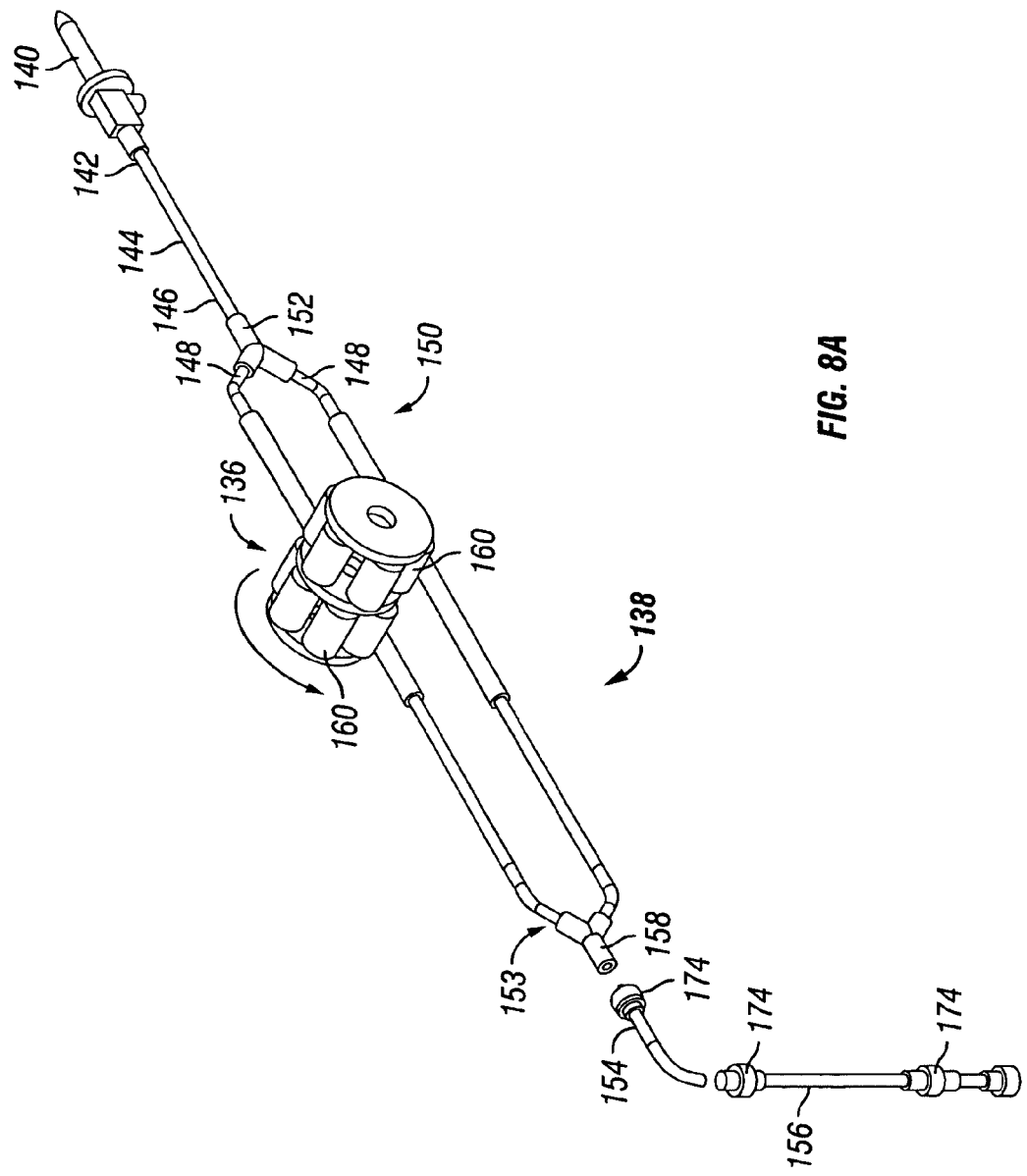
FIGS. 8A and 8B illustrate perspective views of tubing sets in accordance with an embodiment of the present invention.

In addition to a single peristaltic pump 130 or gear cartridge 132, the injection system of the present invention may include multiple peristaltic pumps 130 or gear cartridges 132, including combinations thereof. In one embodiment of the invention, a peristaltic pump having two rotors 136 is used to transport fluid through the tubing set. Referring to FIG. 8A, one embodiment of a tubing set 138 used with a double rotor peristaltic pump includes a spike 140 in fluid communication with a proximal end 142 of a first single lumen portion 144 of the tubing segment. The distal end 146 of the single lumen portion 144 connects to a proximal end 148 of a two-lumen portion 150 of the tubing set 138 via a first T-connector or Y-connector 152. In addition, the distal end 153 of the two-lumen portion 150 then connects to a proximal end 154 of a second single lumen portion 156 of the tubing set 138 via a second T-connector or Y-connector 158. It should be noted that the distal end of the second single lumen portion 156 of the tubing set 138 corresponds to the patient end of the system.

As shown in FIG. 8A, each rotor 136 of the double rotor peristaltic pump is aligned on each lumen of the two-lumen portion 150 of the tubing set 138. In addition, the rollers 160 of the first rotor are out of alignment with the rollers 160 of the second rotor. As such, during use, rotation of the rollers 160 causes fluid to be drawn from the reservoir (not shown) through the spike 140 and into the first single lumen portion 144 of the tubing set 138. Fluid then flows through the Y-connector 152 and into the two-lumen portion 150 of the tubing set 138. Any pulses, gaps or breaks in the column of fluid in the tubing are reduced or eliminated via the peristaltic pump. In particular, as the fluid flows through the tubing portion 150 under the rotors 136, the rollers 160 compress alternating segments of the tubing and, thereby, function similar to a full-wave rectifier. As such, pulses, gaps or breaks in the column of fluid are eliminated when the fluid flows through the second Y-connector 158 and into the second single lumen portion 156 of the tubing set 138. In addition, the double rotor peristaltic pump also increases fluid flow rate without requiring an increase in tubing size.

Figure 8B:
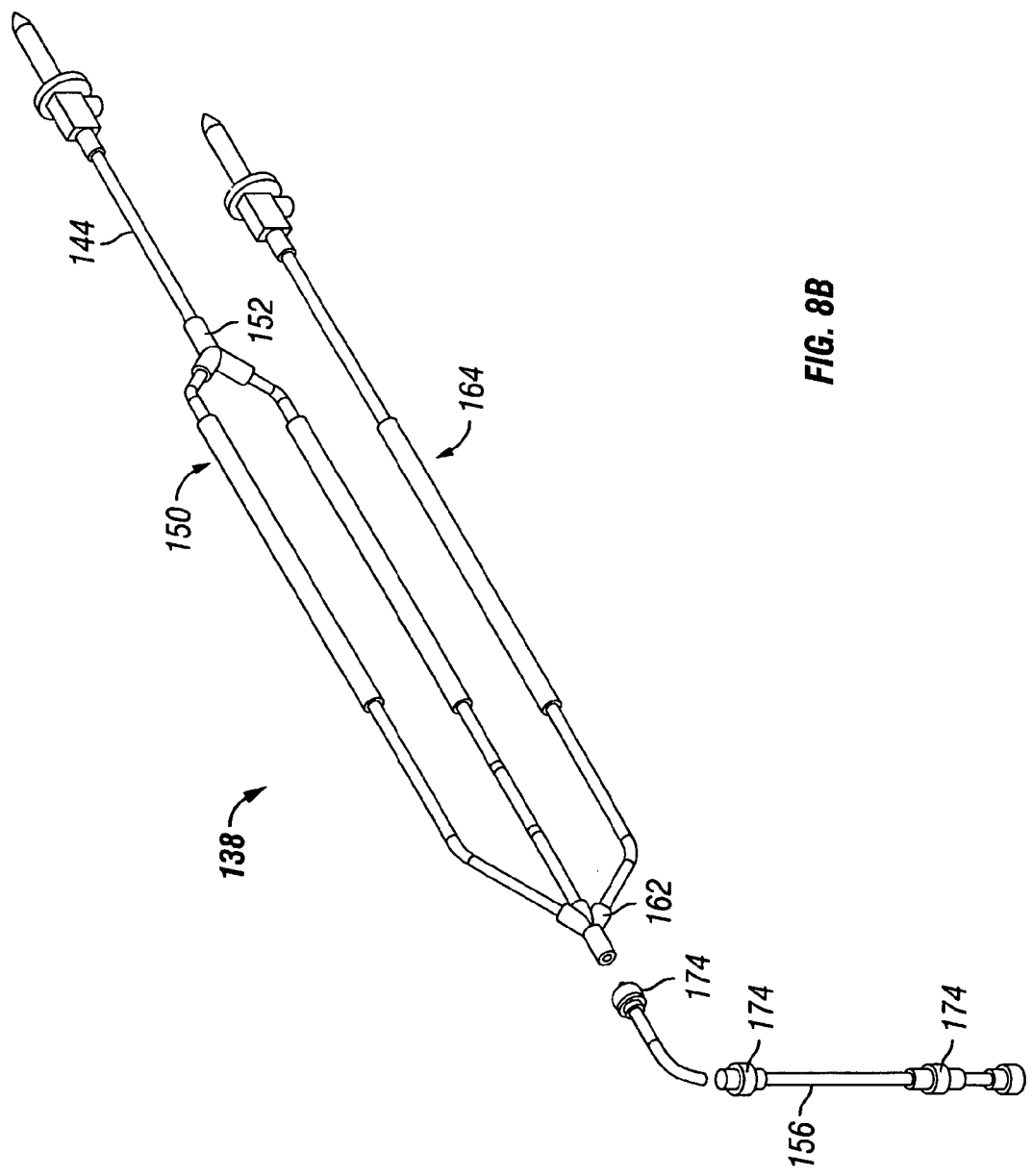

In an alternate embodiment, the second T-connector or Y-connector 150 of the tubing set 138 illustrated in FIG. 8A is replaced with a 3-way Y-connector 162. As shown in FIG. 8B, a third single lumen tubing portion 164 is joined to the tubing set 138 via the 3-way Y-connector 162. This tubing set embodiment provides an additional lumen to accommodate a different fluid type (for example, saline) and fluid flow rate, as described in further detail below.

Figure 9A:
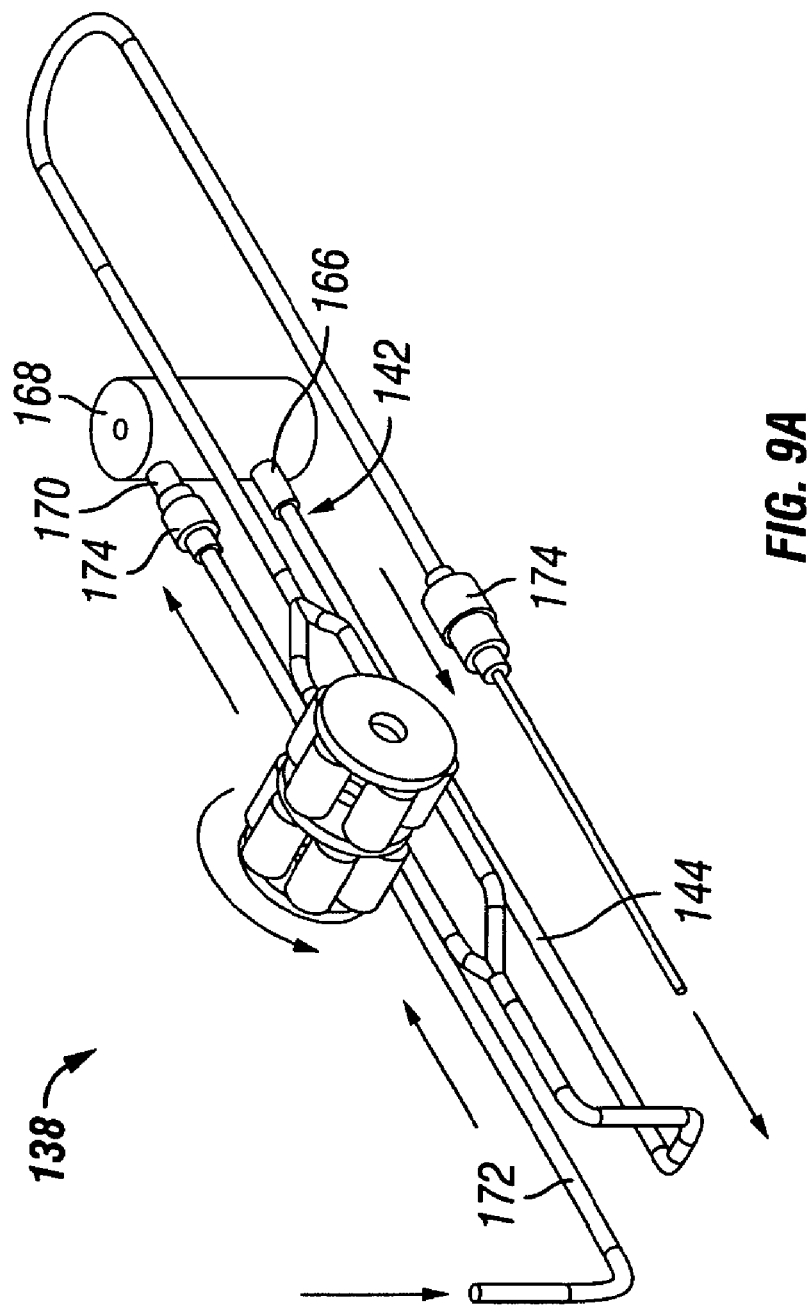
FIGS. 9A and 9B illustrate perspective views of tubing sets in accordance with an embodiment of the present invention.
Figure 9B:
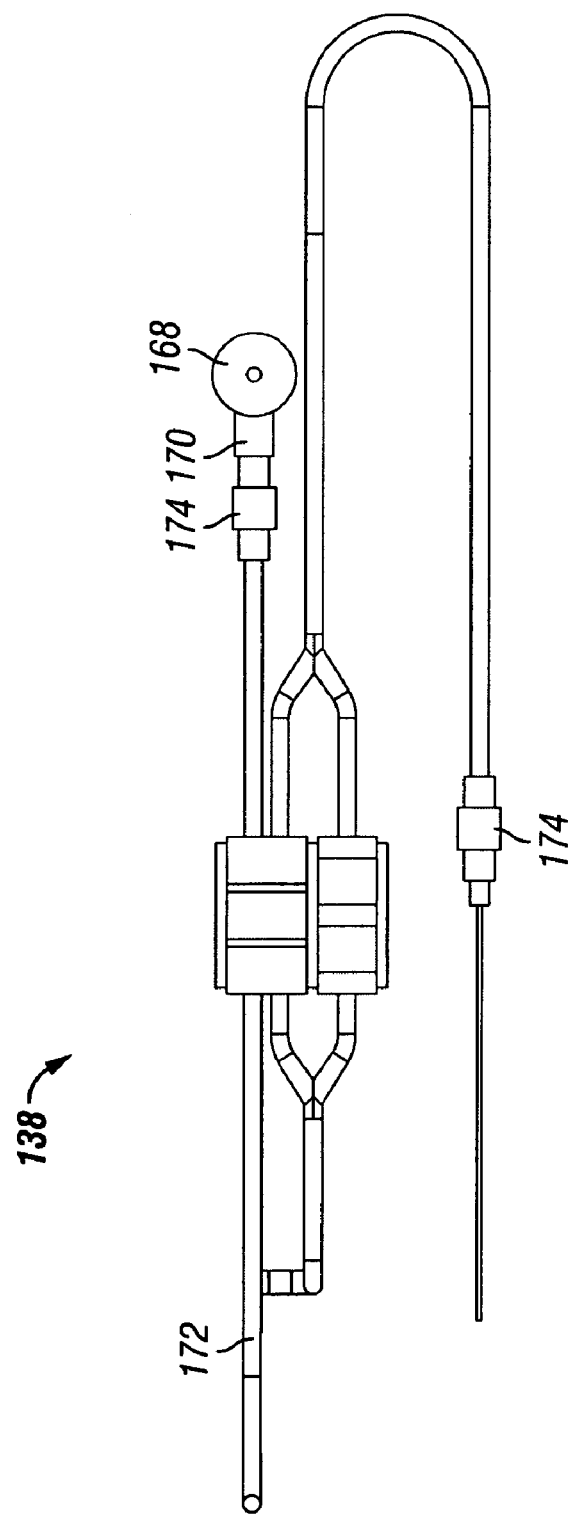

An alternate embodiment of a tubing set 138 used with the device of the present invention is shown in FIGS. 9A and 9B. The tubing set 138 illustrated in FIGS. 9A and 9B is similar to the tubing set illustrated in FIGS. 8A and 8B. However, the proximal end 142 of the first single lumen portion 144 of the tubing set is in fluid communication with a lower port 166 of a holding chamber 168, rather than a spike 140 as with the previous embodiment of the invention. In addition, an upper port 170 of the holding chamber 168 is in fluid communication with a third single lumen portion 172 of the tubing set 138. The proximal end of the third single lumen portion 172 connects to the reservoir (not shown) of the system. In general, this embodiment of the tubing set 138 functions similar to the previous embodiment. However, the holding chamber 168 has been added to act as a fluid accumulator and to lessen the sinusoidal effect of the pump rollers on the third single lumen portion 172. In addition, the holding chamber 168 provides an air gap or break in the fluid stream (similar to a drip chamber) and, thereby, acts as an extra-safety device that separates reusable and disposable components, as described in further detail below.

During use, the peristaltic pump draws fluid from the reservoir (not shown) through the third single lumen portion 172 and into the holding chamber 168. The fluid then drains along the inner sidewall and accumulates at the bottom of the holding chamber 168. The same peristaltic pump then draws fluid from the holding chamber through the remaining portions of the tubing set and into the patient.

In yet another embodiment of the invention, one or more check valves may also be added to the tubing set of the present invention. Referring to FIGS. 9A and 9B, a check valve 174 is located on the third single lumen tubing portion 172 near the upper port 170 of the holding chamber 168. As such, all components from the check valve forward (i.e., downstream of the check valve 174), including the check valve 174, are single use components and are discarded after each patient procedure or use. In contrast, all components in back of the check valve 174 (i.e., upstream from the check valve 174) are multiple use components and may be reused on one or more patients or cases. In general, the check valve 174 may be positioned at any location on the tubing set 138. However, as previously described, all components in front of and in back of the check valve 174 are single use and multiple use components, respectively. This particular tubing configuration provides additional cost benefits and contributes to user convenience when using the injector system of the present invention.

Figure 10:
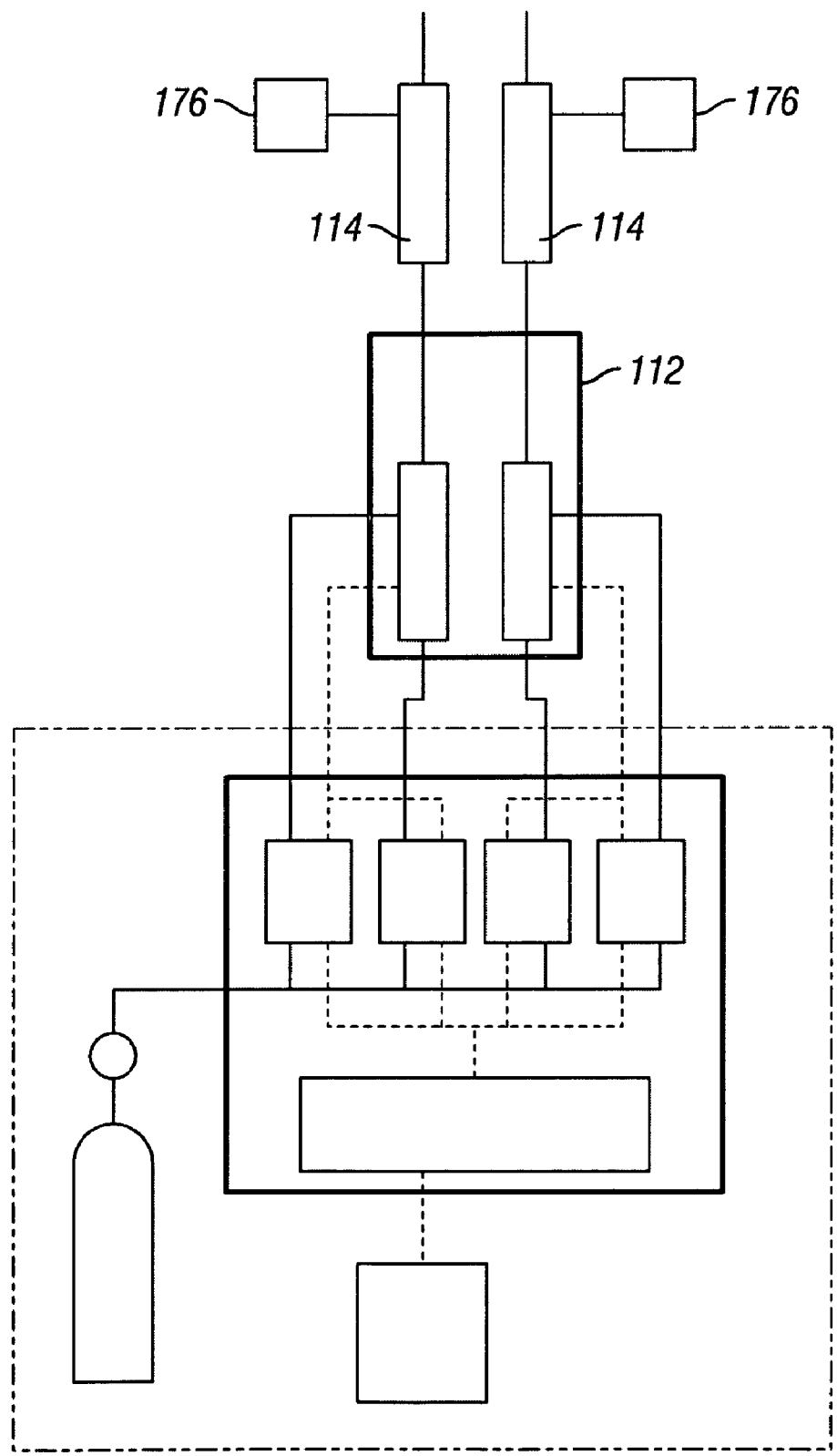
FIG. 10 is a block diagram illustrating an injector system in accordance with an embodiment of the present invention.

In an alternate embodiment of the invention, shown in FIG. 10, more than one cylinder assembly 112 may be used with the device of the present invention. In addition, each cylinder assembly 112 may also be connected to a separate syringe assembly 114. As such, different fluids, for example contrast media and saline, may be injected into the patient using only one injection system and without requiring multiple system set-ups during the procedure. Further, a variety of injection procedures may be performed with this embodiment of the invention via the control valves. For example, one procedure may require simultaneous actuation of the valves so that both saline and contrast material are injected into the patient. The flow rates of each fluid may also be individually controlled, thereby providing different concentrations of contrast media and saline. Alternatively, an injection procedure may require a series of saline and contrast media injections, thereby requiring serial actuation of the control valves. As before, the flow rate of each fluid may be individually controlled to properly execute the desired procedures. Additional injection procedures, not specifically disclosed herein, are also included within the scope of the present invention.

Figure 11:
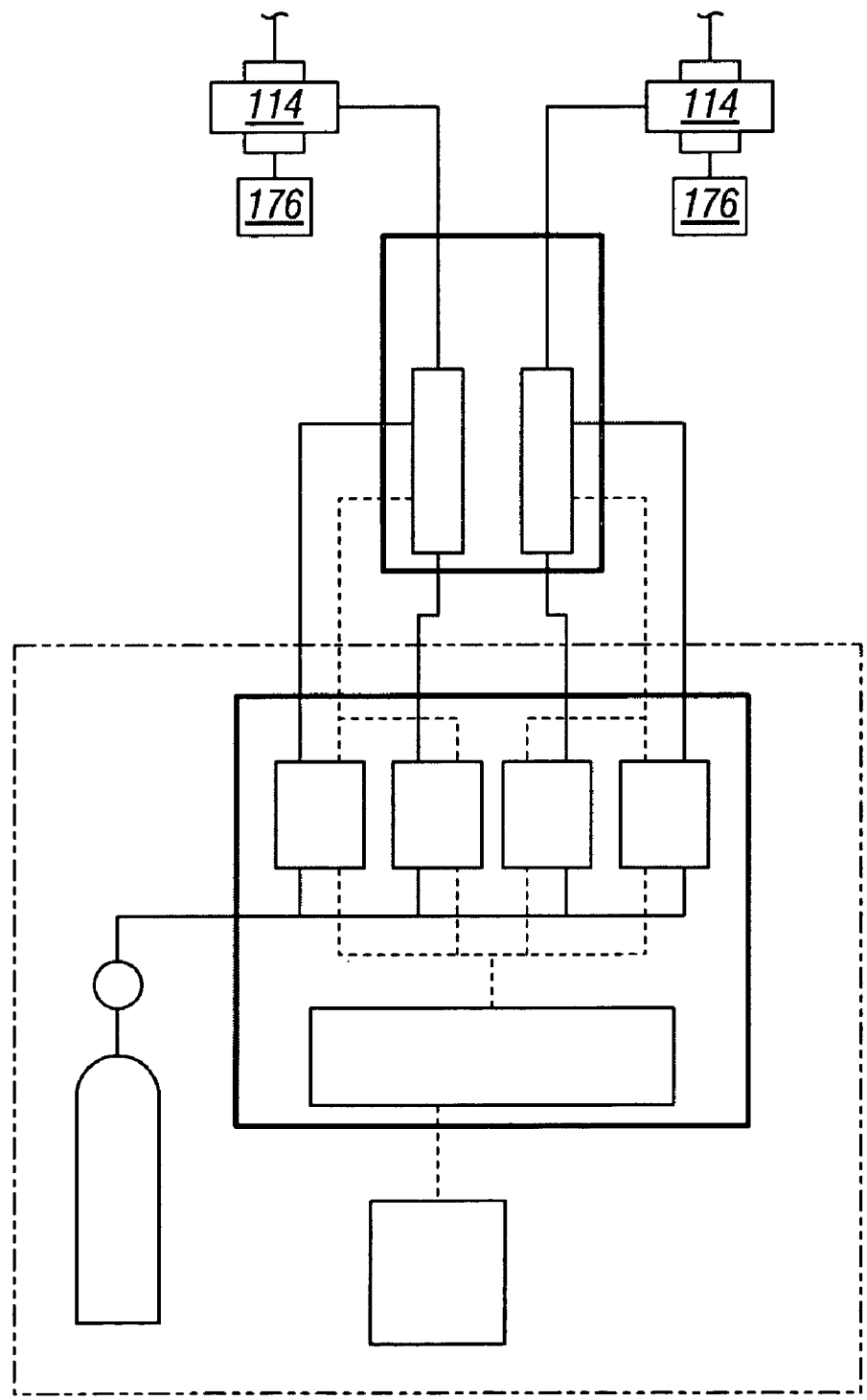
FIG. 11 is a block diagram illustrating an injector system in accordance with an embodiment of the present invention.

Multiple cylinder/syringe assemblies may also be used to form an alternate embodiment of a continuous flow injection device. As shown in FIG. 10, fluid from the reservoir 176 flows into the syringe body 114 via a single port. Movement of the syringe plunger in the distal direction forces fluid out of the syringe 114 and into the tubing, whereas proximal movement of the syringe 114 draws fluid from the reservoir and into the syringe body. As such, this configuration of the invention may produce intermittent injections due to the syringe filling phase of the procedure. However, a continuous injection procedure may be performed by sequencing actuation of the fluid control valves and using a Y-shaped tubing set. For example, referring to FIG. 11, as a first syringe 114 is drawing in fluid from its reservoir 176, the second syringe 114 may be forcing fluid out to the tubing set. Likewise, as the first syringe 114 is forcing fluid out to the tubing set, the second syringe 114 may be drawing in fluid from its reservoir 176 to refill the second syringe 114. Since the tubing sets from each syringe join to form a single tube that connects to the patient, this configuration produces a continuous flow of fluid or fluid injection into the patient. It should also be noted that either separate reservoirs or one common reservoir may be used with this embodiment of the invention.

Figure 12:
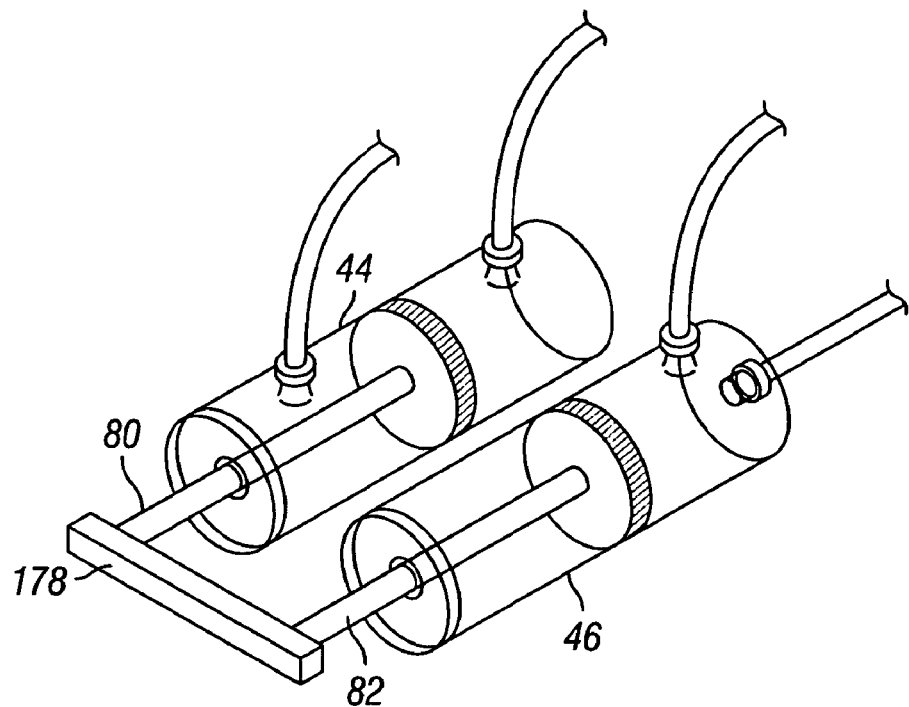
FIG. 12 is a perspective view of a cylinder assembly and syringe assembly in accordance with an embodiment of the present invention.
Figure 13:
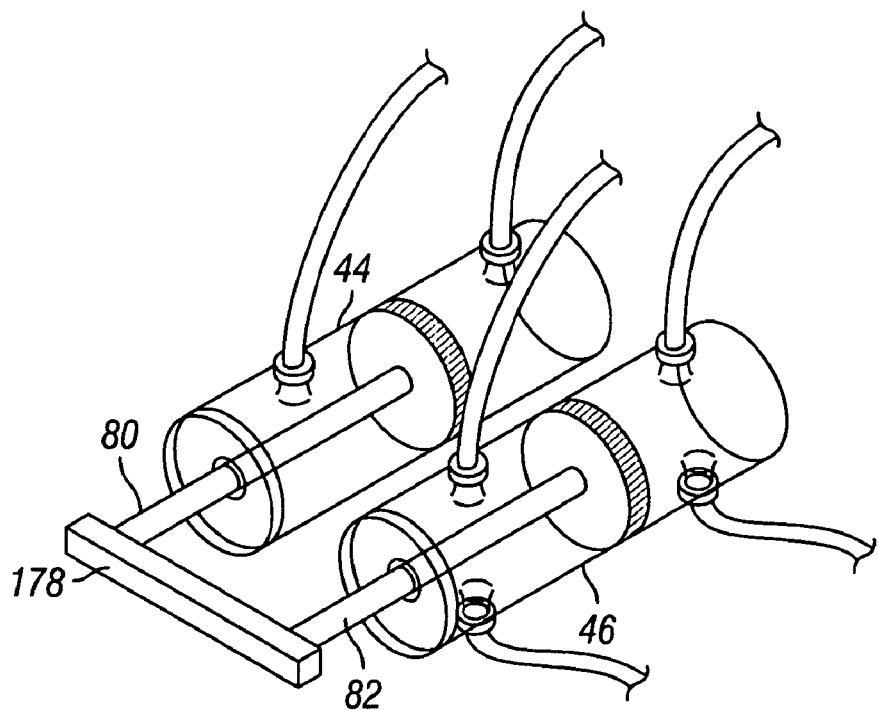
FIG. 13 is a perspective view of a cylinder assembly and syringe assembly in accordance with an embodiment of the present invention.

In addition to linear arrangements of the cylinder and syringe assemblies, examples of which are illustrated in FIGS. 3 and 4, a variety of non-linear configurations may also be used. For example, referring to FIGS. 12 and 13, the cylinder and syringe assemblies may be in parallel alignment whereby the cylinder assembly 44 is located adjacent to the syringe assembly 46 of the injector system. However, unlike the previously described embodiments wherein the plunger shafts extend from the distal and proximal ends of the cylinder and syringe assemblies, respectively, the plunger shafts 80,82 in this embodiment of the invention extend from the distal ends of both the cylinder 44 and syringe 46 assemblies. In addition, as shown in FIGS. 12 and 13, a bar or rod 178 connects the shafts 80,82 together so that movement of the cylinder plunger simultaneously drives the syringe plunger.

Figure 14A:
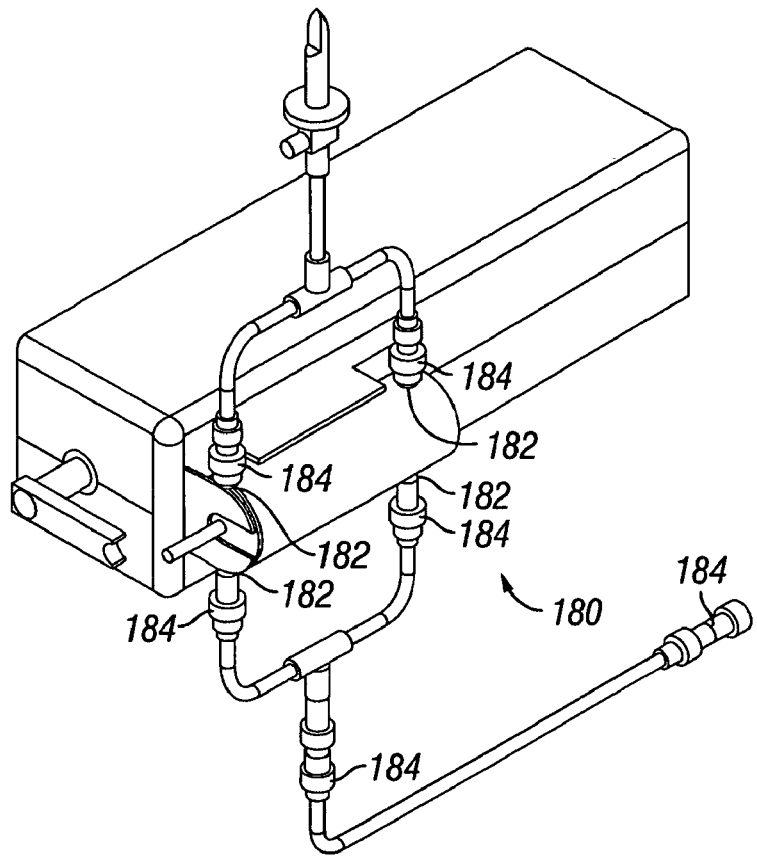
Figure 14B:
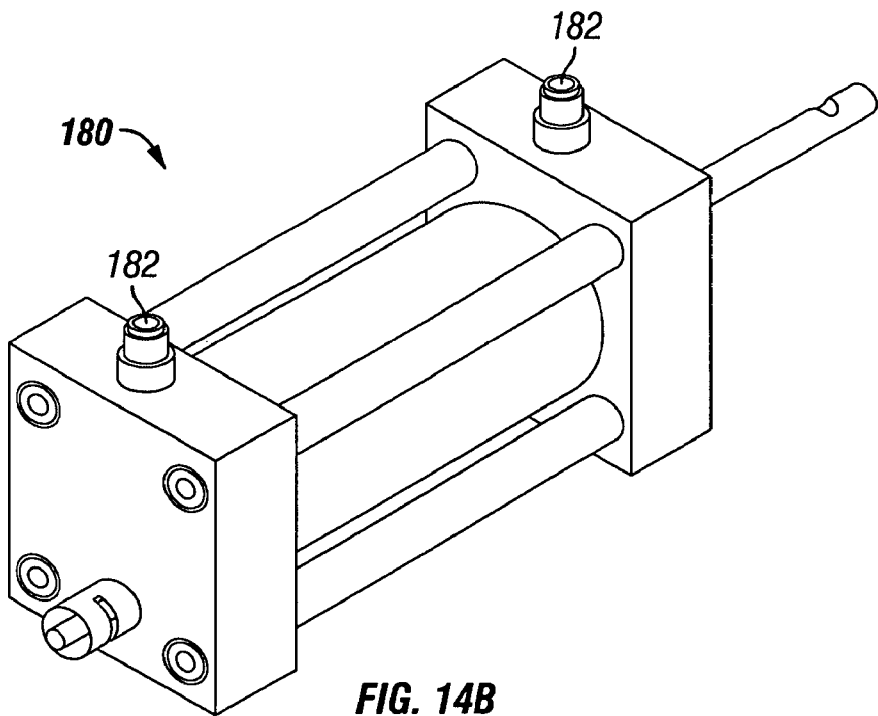
Figure 14D:
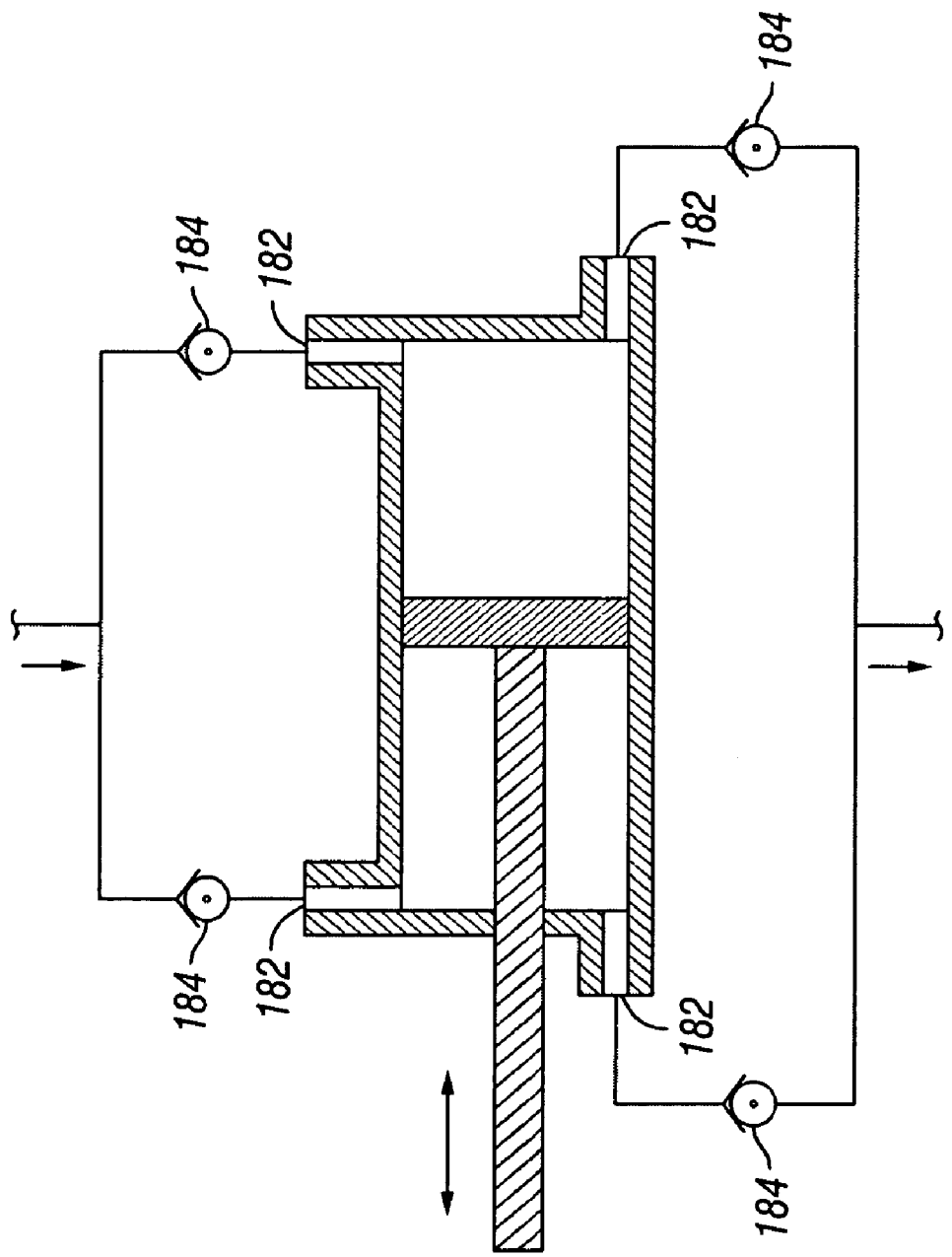

Various syringe assembly and cylinder assembly designs may also be used with the injector system of the present invention. One example of a suitable syringe assembly design is illustrated in FIGS. 14A-D. In this embodiment, the syringe assembly 180 includes four ports 182, with two ports located near the proximal end and two ports located near the distal end of the syringe assembly 180. However, different numbers and locations of ports 182 may also be used and are included within the scope of the claimed invention. One or more valves 184 located adjacent each port 182 to control fluid flow may also be used. As shown in FIG. 14D, movement of the syringe plunger draws fluid from the reservoir (not shown), through a first port 182 having an open valve 184 and into a first sub-chamber of the syringe body. Reciprocal movement of the syringe plunger draws fluid from the reservoir, through a second port 182 having an open valve 184 and into a second sub-chamber of the syringe body. In addition, fluid is also being forced out of the first sub-chamber, through a third port 182 having an open valve 184 and to the patient. Continued reciprocal movement of the syringe plunger once again draws fluid from the reservoir into the first sub-chamber and, also, forces fluid out of the second sub-chamber, through a fourth port 182 of the syringe and to the patient. As such, this continuous-flow syringe configuration contributes to user and patient convenience by not requiring a separate filling phase, which would produce intermittent injections or delays during the injection procedure. Further, the system design also provides additional cost benefits through more efficient use of fluids, such as contrast media.

Figure 15A:
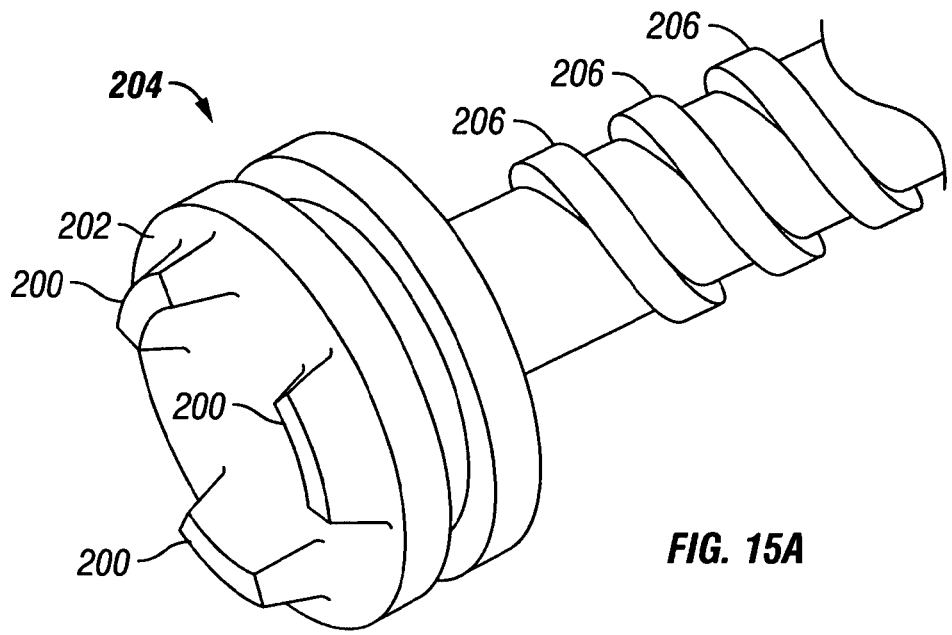
FIG. 15A is a perspective view of a portion of a syringe plunger assembly in accordance with an embodiment of the present invention.

An alternate embodiment of the syringe assembly is also shown in FIG. 15. Some procedures used with the injector system 10 of the present invention may require fluid agitation, for example, to disperse bubbles in the fluid. As such, one or more blades, vanes or mixing paddles 200 are formed on a fluid contacting surface 202 of the plunger wiper 204 and threads 206 are included on the plunger shaft 208. During use, the linear motion or force generated from the shaft of the second cylinder assembly (not shown) is transferred to the plunger shaft 208 and translated into rotational motion via the threads 206 of the plunger shaft 208. Thus, as the threads 206 contact the mating element of the syringe assembly (not shown), the shaft 208 and, thereby, wiper 204 rotate. Rotation of the wiper 204 agitates the fluid via the blades 200, similar to a propeller on a boat. The threads 206 of the plunger shaft 208 may also generate additional fluid agitation.

Figure 15B:
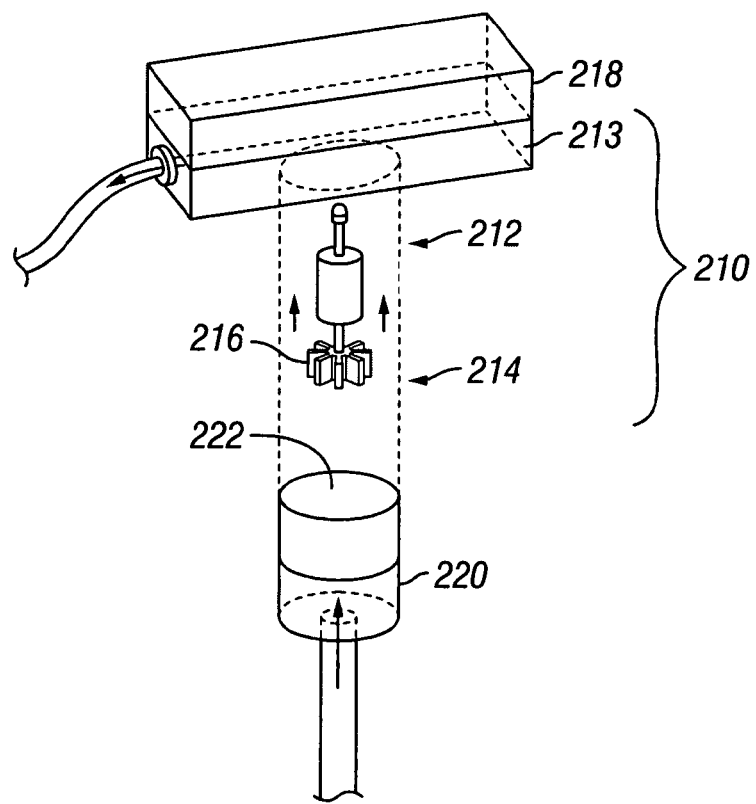
FIG. 15B illustrate an embodiment of a rotary vane pump assembly in accordance with an embodiment of the present invention.

In yet another embodiment of the invention, rotary forces generated by a motor, a hydraulic system or a pneumatic system may be used to pump fluid from a reservoir and into the patient. As shown in FIG. 15B, a rotary vane pump 210 includes a distal end 212, a proximal end 214 and a housing 213 in fluid communication with a patient (not shown). The proximal end 214 of the pump 210 includes one or more vanes, blades or paddles that form a propeller 216 of the device. The distal end 212 of the pump 210 connects to the motor 218 which may be hydraulically, pneumatically or electrically driven. A portion of the pump 210, in particular the proximal end 214 of the pump 210, is housed within a cartridge 220 that forms a fluid chamber 222 and is in fluid communication with a reservoir (not shown). During use, rotation of the pump 210 and, thereby, the propeller 216 draws fluid from a reservoir into the cartridge chamber 222 and out of the pump 210 to the patient. As such, the pump 210 functions similar to the gear cartridge as previously described.

Figure 16:
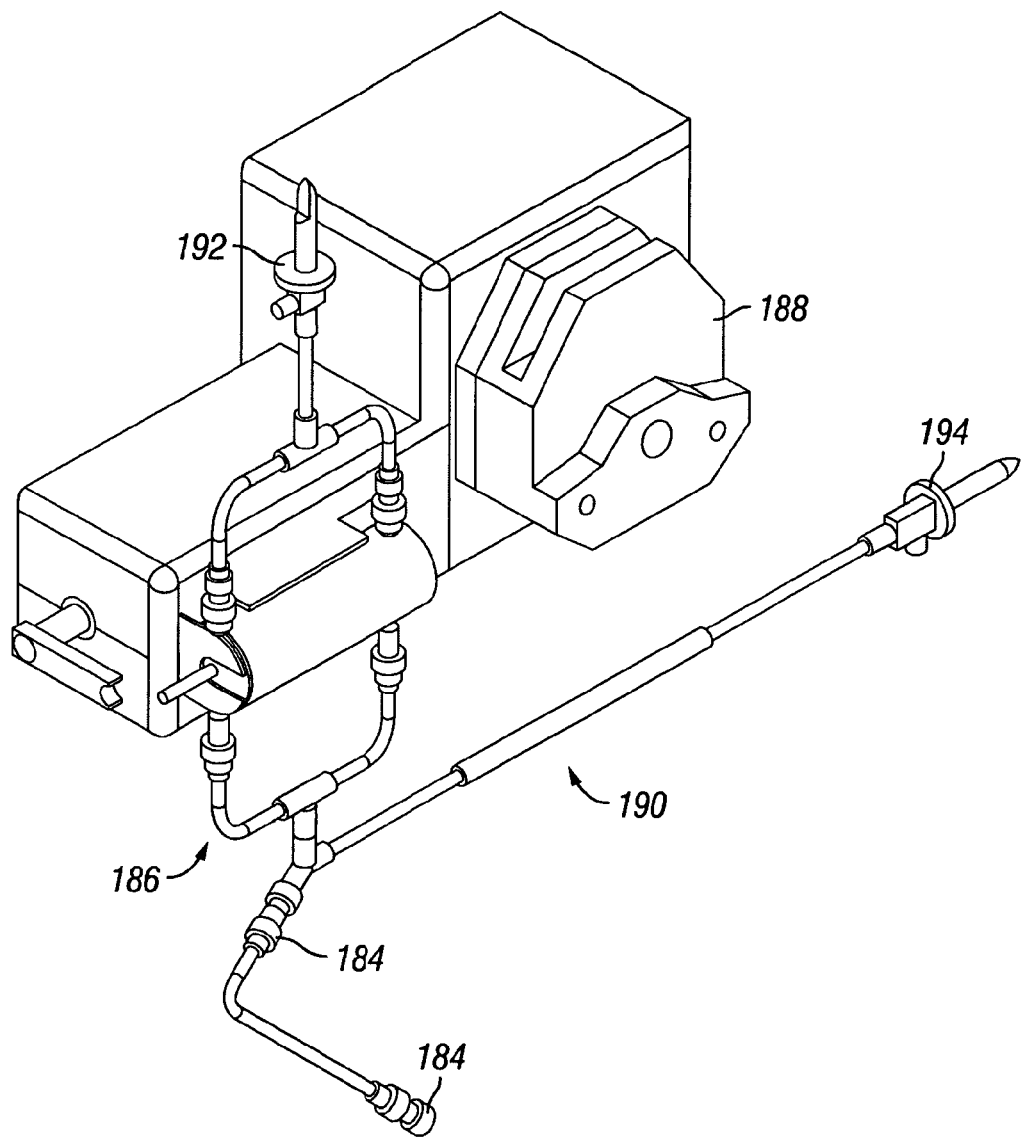
FIG. 16 is a perspective view of a module of an injector system in accordance with an embodiment of the present invention.

In an alternate embodiment of the invention, the injector system may include various combinations of the above-referenced assemblies and components. For example, as shown in FIG. 16, a portion or module of the injector system may include a hydraulic/pneumatic controlled syringe assembly 186 and peristaltic pump assembly 188. Each assembly may be individually controlled via cylinders, motors and/or valves. The tubing set 190, similar to those previously described (e.g., as shown in FIG. 8B), permits fluid combinations of varying concentrations to be injected into a patient. For example, one spike 192 of the tubing set may be connected to a contrast media reservoir and the other spike 194 may be attached to a saline reservoir. Thus, this multifunction injector module accommodates one or more fluid types, performs cost-effective, continuous injection procedures at variable fluid flow rates and concentrations and, further, provides a safe and efficacious alternative to conventional injection systems.

It is noted that the foregoing different embodiments of the present invention were illustrated separately at times for the purpose of brevity and reader convenience. As such, any process or system using one or more of the disclosed embodiments, including embodiments not specifically disclosed herein, is also included within the scope of the claimed invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of injecting a first fluid into a patient during a magnetic resonance imaging procedure, said method comprising:
   providing communication between a cylinder assembly in a control room of an imaging facility and a console in said control room, said console comprising a user control device;
   providing communication between a hydraulic motor in a patient room of said imaging facility and a peristaltic pump in said patient room;
   providing communication between said cylinder assembly in said control room and said hydraulic motor in said patient room;
   driving said cylinder assembly with a motor of said console;
   providing a second fluid from said cylinder assembly under pressure;
   driving said hydraulic motor with said second fluid that is fed through said hydraulic motor to cause said hydraulic motor to generate rotary forces;
   driving said peristaltic pump with said rotary forces generated by said hydraulic motor; and
   injecting said patient with said first fluid using said peristaltic pump.

2. The method of claim 1, wherein said injecting of said first fluid is caused by rotation of a rotor of said peristaltic pump which causes rollers of said rotor to compress a tubing, thereby drawing in said first fluid and transporting said first fluid through said tubing and into said patient.

3. A method of injecting a first fluid into a patient during a magnetic resonance imaging procedure, said method comprising:
   providing communication between a cylinder assembly in a control room of an imaging facility and a console in said control room, said console comprising a user control device;
   providing communication between a hydraulic motor in a patient room of said imaging facility and a gear cartridge in said patient room;
   providing communication between said cylinder assembly in said control room and said hydraulic motor in said patient room;
   driving said cylinder assembly with a motor of said console;
   providing a second fluid from said cylinder assembly under pressure;
   driving said hydraulic motor with said second fluid that is fed through said hydraulic motor to cause said hydraulic motor to generate rotary forces;
   driving said gear cartridge with said rotary forces generated by said hydraulic motor; and
   injecting said patient with said first fluid using said gear cartridge.

4. The method of claim 3, wherein said injecting of said first fluid is caused by rotation of a rotor which causes gears in said gear cartridge to rotate and compress a tubing located between said gears, thereby drawing in said first fluid and transporting said first fluid through said tubing and into said patient.

5. A system to inject a first fluid into a patient during a magnetic resonance imaging procedure, said system comprising:
- a console in a control room of an imaging facility, said console comprising a user control device;
- a cylinder assembly in said control room of said imaging facility, said cylinder assembly being in communication with said console;
- a peristaltic pump in a patient room of said imaging facility; and
- a hydraulic motor in said patient room of said imaging facility, said hydraulic motor being in communication with said cylinder assembly and said peristaltic pump,
- wherein a motor of said console drives said cylinder assembly,
- wherein said hydraulic motor is driven with a second fluid that is provided from said cylinder assembly under pressure,
- wherein said second fluid is fed through said hydraulic motor to cause said hydraulic motor to generate rotary forces that drive said peristaltic pump, and
- wherein said peristaltic pump injects said first fluid into said patient.

6. A system to inject a first fluid into a patient during a magnetic resonance imaging procedure, said system comprising:
- a console in a control room of an imaging facility, said console comprising a user control device;
- a cylinder assembly in said control room of said imaging facility, said cylinder assembly being in communication with said console;
- a gear cartridge in a patient room of said imaging facility; and
- a hydraulic motor in said patient room of said imaging facility, said hydraulic motor being in communication with said cylinder assembly and said gear cartridge,
- wherein a motor of said console drives said cylinder assembly,
- wherein said hydraulic motor is driven with a second fluid that is provided from said cylinder assembly under pressure,
- wherein said second fluid is fed through said hydraulic motor to cause said hydraulic motor to generate rotary forces that drive said gear cartridge, and
- wherein said gear cartridge injects said first fluid into said patient.

* * * * *